United States Patent [19]

Higashikawa

[11] Patent Number: 5,704,918
[45] Date of Patent: Jan. 6, 1998

[54] SYRINGE

[76] Inventor: Tetsuro Higashikawa, 21-5, Kamimeguro 5-chome, Meguro-ku, Tokyo 153, Japan

[21] Appl. No.: 766,913

[22] Filed: Dec. 13, 1996

Related U.S. Application Data

[62] Division of Ser. No. 446,832, filed as PCT/JP93/01742 Nov. 30, 1993, Pat. No. 5,599,312.

[30] Foreign Application Priority Data

| Dec. 1, 1992 | [JP] | Japan | .................. 4-343610 |
| Dec. 16, 1992 | [JP] | Japan | .................. 4-353880 |
| Feb. 10, 1993 | [JP] | Japan | .................. 5022736 |

[51] Int. Cl.$^6$ .................................................. A61M 5/00
[52] U.S. Cl. .................................................. 604/191
[58] Field of Search ........................ 604/191, 89, 90, 604/218, 232

[56] References Cited

U.S. PATENT DOCUMENTS

| 3,680,558 | 8/1972 | Kapelowitz . |
| 3,749,084 | 7/1973 | Cucchiara . |
| 4,235,235 | 11/1980 | Bekkering . |
| 4,439,184 | 3/1984 | Wheeler . |
| 4,496,344 | 1/1985 | Kamstra . |
| 4,668,223 | 5/1987 | Grotenhuis . |
| 4,929,230 | 5/1990 | Pfleger . |

FOREIGN PATENT DOCUMENTS

| 0 144 551 | 8/1984 | European Pat. Off. . |
| 0 245 895 | 11/1987 | European Pat. Off. . |
| 0 511 402 | 11/1992 | European Pat. Off. . |
| 0 520 618 | 12/1992 | European Pat. Off. . |
| 2 354 781 | 1/1978 | France . |
| 2 573 310 | 5/1986 | France . |
| 60-72561 | 4/1985 | Japan . |
| 62-58745 | 12/1987 | Japan . |

*Primary Examiner*—John D. Yasko
*Attorney, Agent, or Firm*—Lowe, Price, LeBlanc & Becker

[57] ABSTRACT

In medical scenes requiring emergency, where plural medicines are to be injected simultaneously, or solution of solid medicine is to be injected, different kinds of injection agents, without being previously mixed, are accommodated in chambers formed separately in a cylinder. In using a syringe, both injection agents can be sequentially injected separately or mixedly by a simple operation.

18 Claims, 24 Drawing Sheets

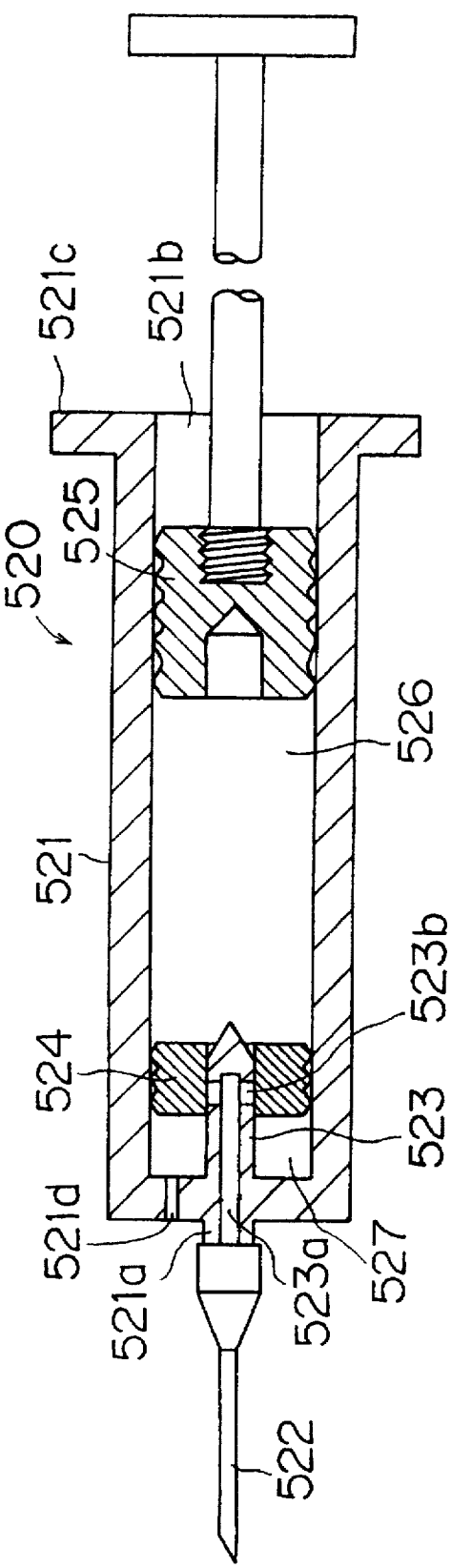
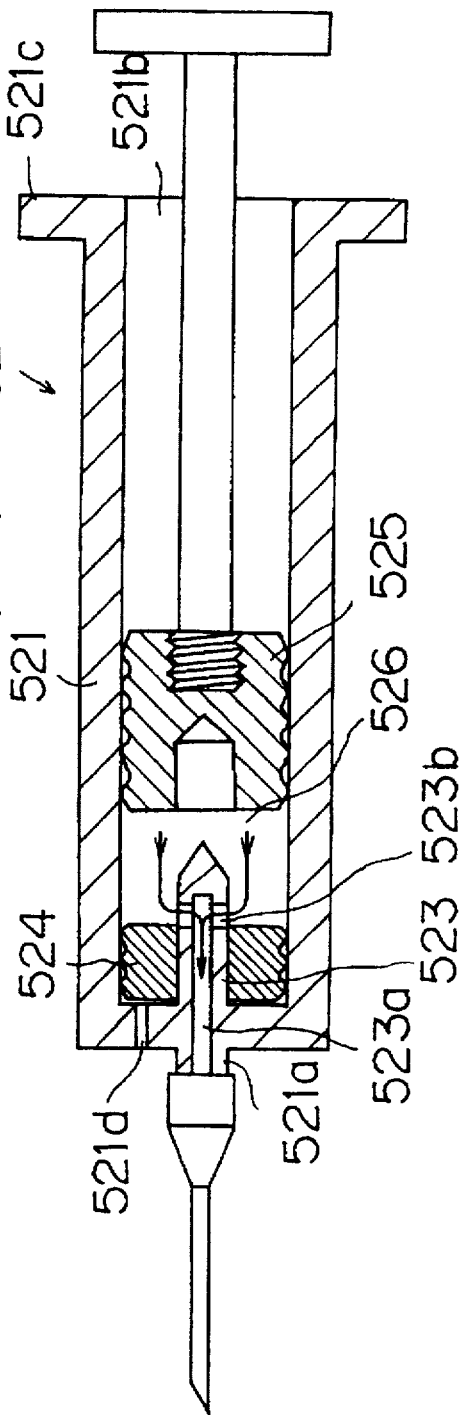

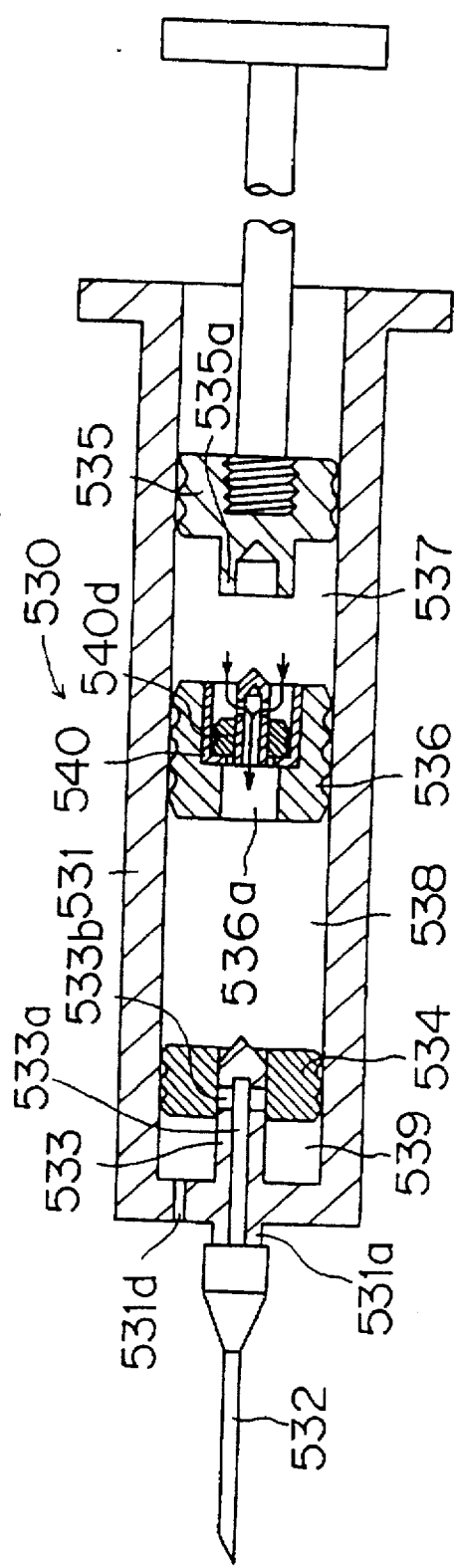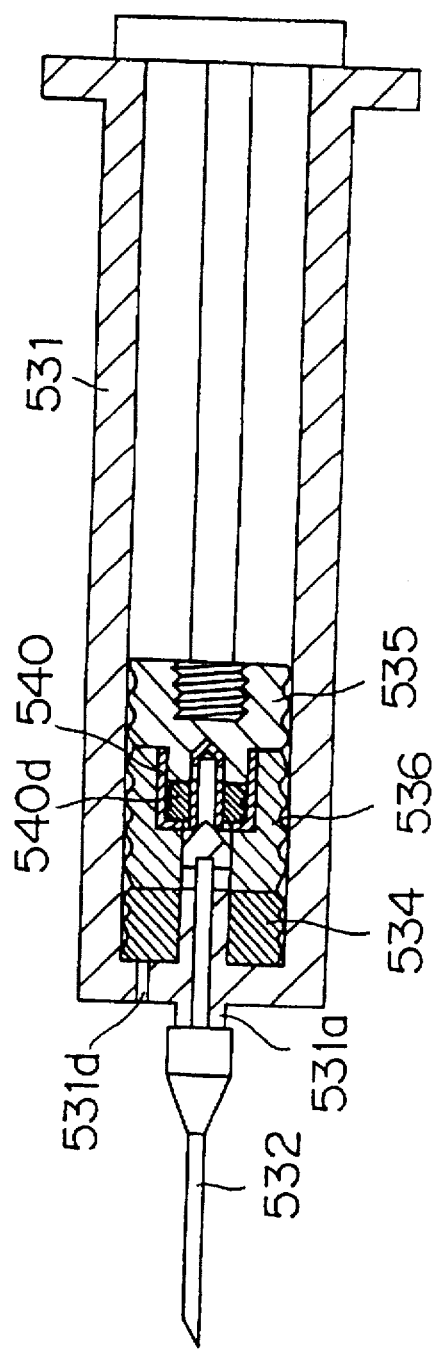

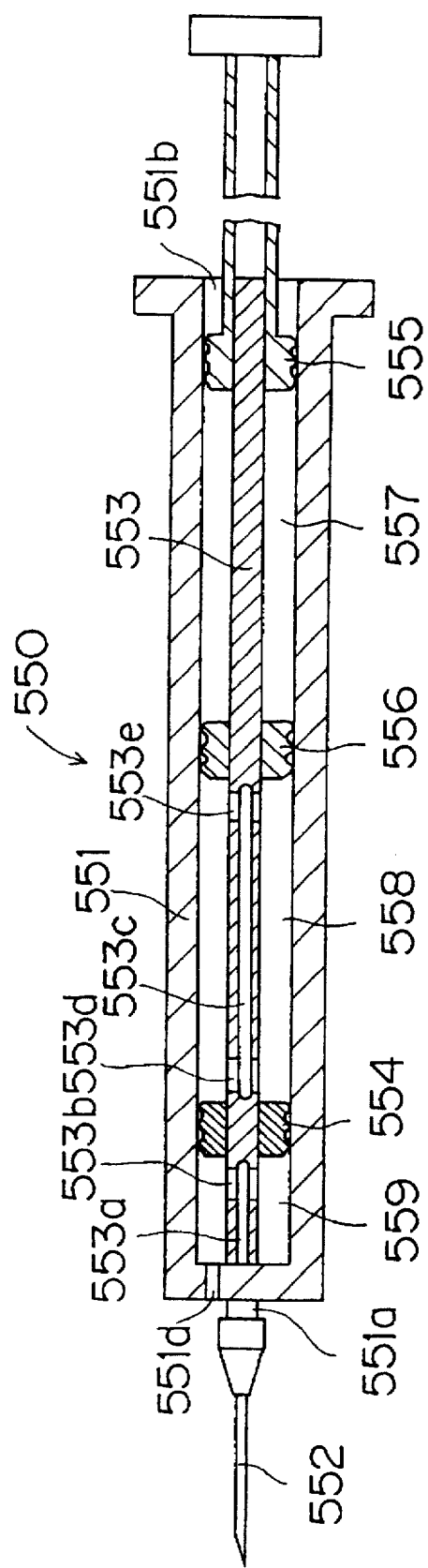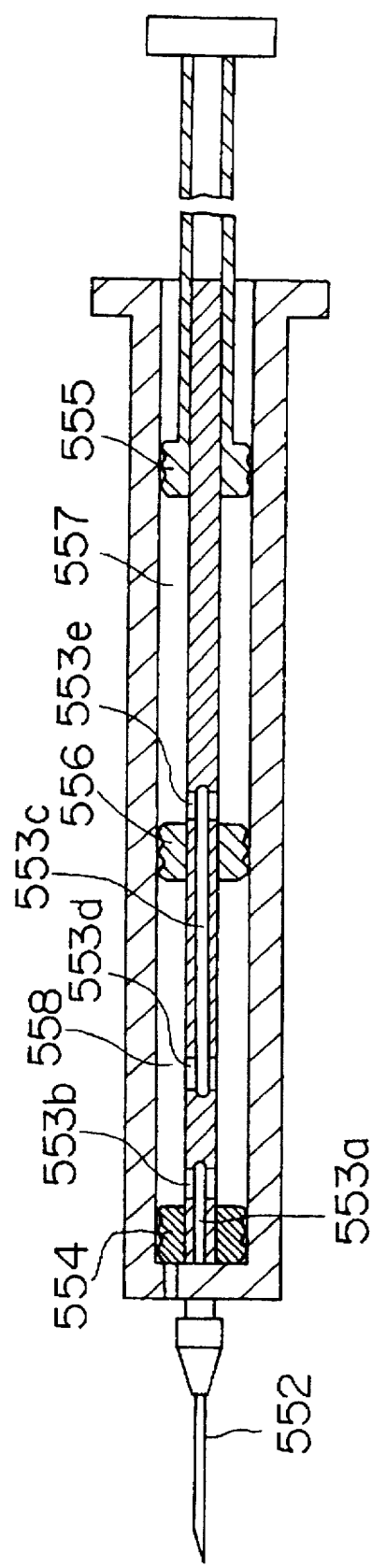

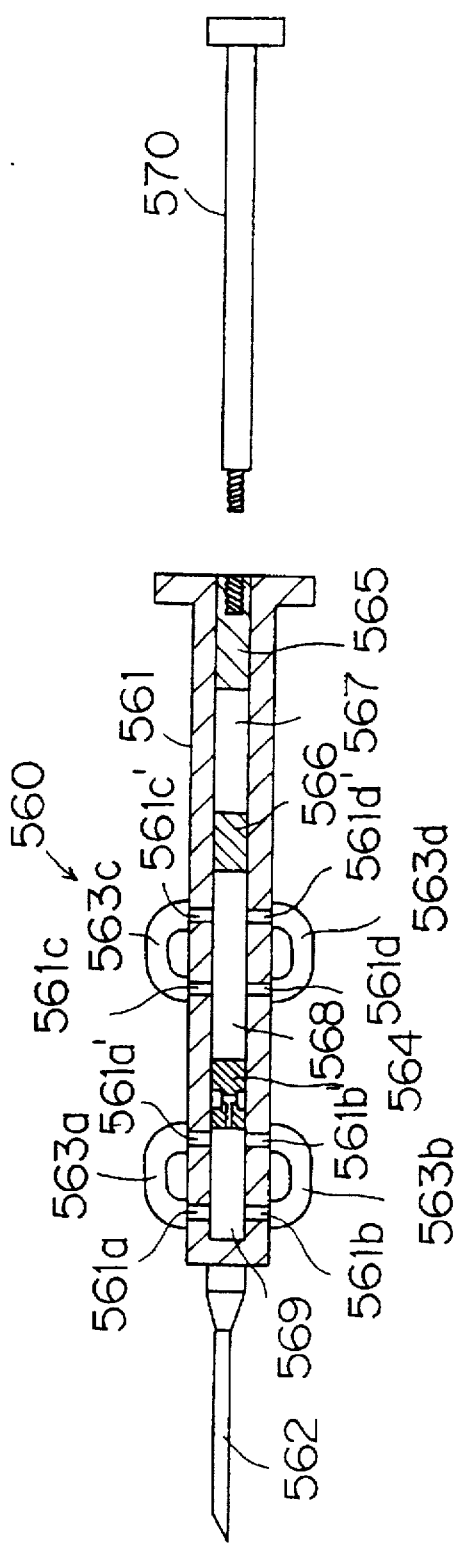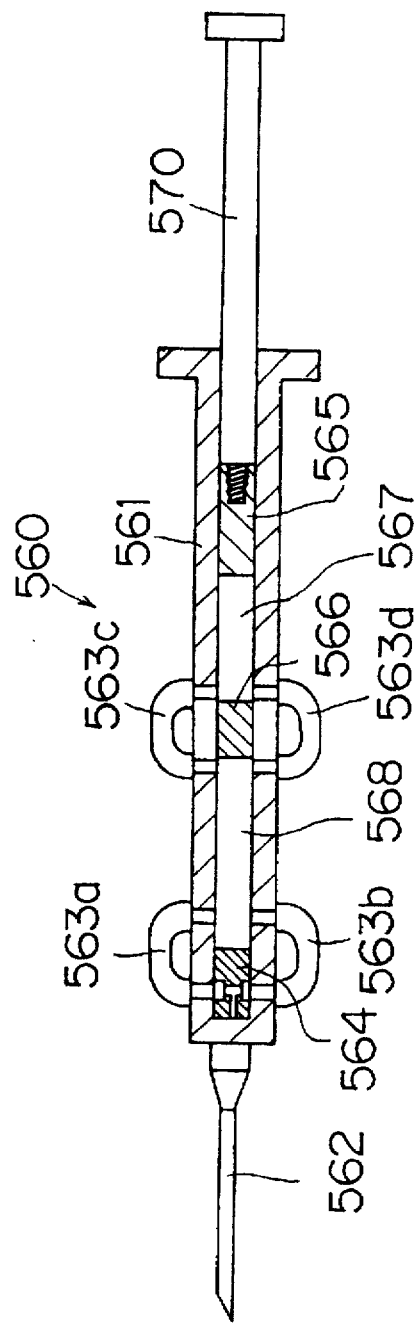
FIG. 22(a)
FIG. 22(b)

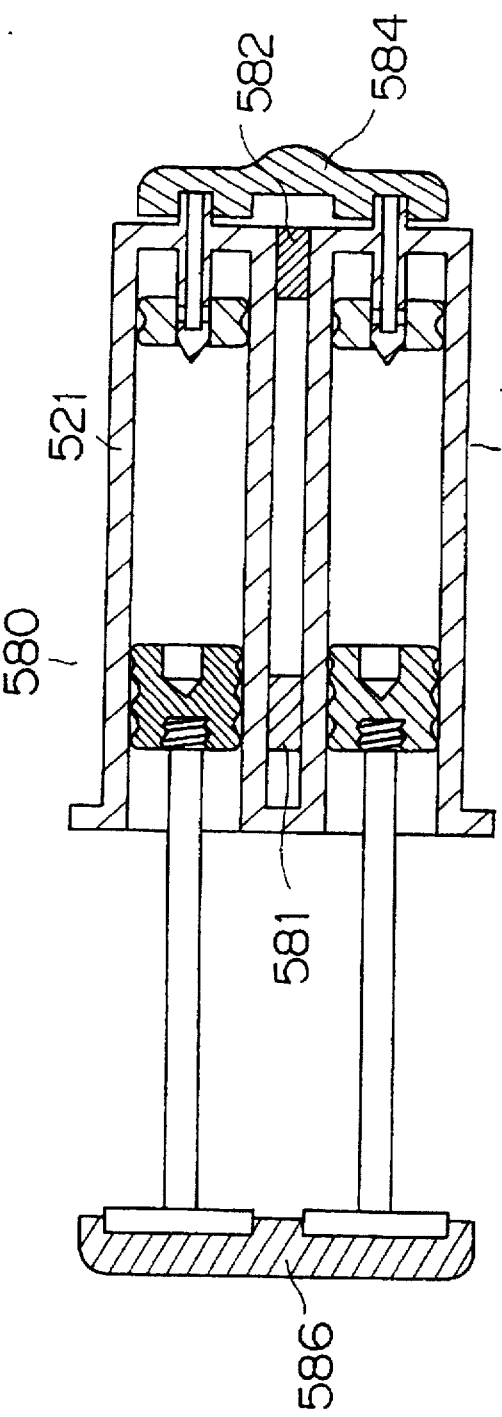
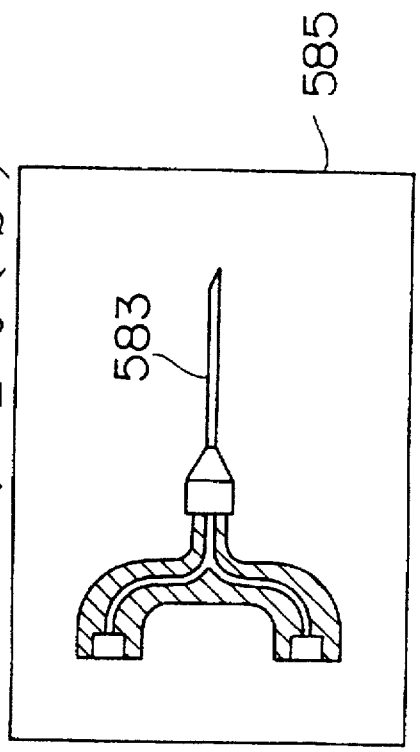
FIG. 26(a)
FIG. 26(b)

SYRINGE

This application is a division of application Ser. No. 08/446,832, filed as PCT/JP93/01742 Nov. 30, 1993 now U.S. Pat. No. 5,599,312.

FIELD OF THE INVENTION

The present invention relates to a syringe for containing medicine, medicine for animals, medicine for clinical diagnosis, and any medicine using a syringe barrel.

BACKGROUND OF THE RELATED ART

The conventional usual injection is contained in an ampoule or vial. In injection, first, the ampoule is cut, or rubber cap of the vial is bored to absorb the injection liquid, and thereafter the injection is given to a patient. In this case, the syringe is disposed so that a single syringe needle is not used for plural persons, thereby preventing infection of bacteria.

Usually, a single injection is carried out as described above. As the case may be, however, a mixed injection of two or more injections is carried out in the injection for treatment of, for example, knee-joint arthritis, shoulder-joint arthritis. Injection of only the hyaluronic acid natrium as a treatment medicine gives a patient a severe pain. To moderate the pain, hydrochloric acid lidocaine as local anesthesia is mixed with the hyaluronic acid.

Specifically, first, the ampoule is cut to absorb hyaluronic acid contained therein into a syringe. Next, using the syringe needle, the rubber stopper of a vial is bored to absorb the hydrochloric acid in the syringe. Thus, two injections are mixed. This mixed injection is injected into the affected part. Two or more injections are also mixed in the case where freezed-dried material such as antibiotic, steroid, vaccine, etc. or powder filler is sealed in a vial, and its solution or diluted solution is contained in an ampoule. In this case, first, the ampoule is cut to absorb the solution contained in the ampoule into a syringe. The syringe needle is thrust through the rubber stopper of a vial to inject the solution within the syringe into the vial. The syringe needle is once pulled out from the rubber stopper. The vial is shaken to dissolve the freeze-dried substance. The syringe needle is again thrust through the rubber stopper to absorb the solution into the syringe. Thereafter, a patient is given the injection.

In the injection manners as described above, persons engaged in medical treatment may be injured by pieces of glass of the ampoule in cutting the ampoule. Then, infection or contagion of hepatitis or AIDS may also occur owing to bleeding. When the ampoule is cut, minute fragments of glass may be mixed into the injection. Further, when the syringe needle is thrust through the rubber stopper, minute fragments of the rubber may be mixed into the injection. Mixture of these alien substances into a human body was confirmed by a microscope. Bad influence of these alien substances on the human body is problematic.

In order to solve these problems, the syringe as shown in FIGS. 28(a) and 28(b) was proposed which is disclosed in Japanese Patent Publication No. Sho 62-58745. This syringe, as shown in FIG. 28(a), includes a needle holder 1 on the side of a syringe needle and a cylinder 4 closed at its ends by plungers 2 and 3. The needle holder 1 and the cylinder 4 are fabricated separately, and the space formed by the plungers 2 and 3 is previously filled with an injection. In use, as shown in FIG. 28(b), with the cylinder 4 fit in the needle holder 1, the plunger 3 is pushed toward the side of the needle. Then, the plunger 2 is pushed into the needle holder 1 and the injection flows through a passage 6 formed in the needle holder 1 toward the needle.

This syringe does not require necessity of cutting the ampoule, and hence can solve the problems of bacteria infection due to injury in ampul cutting and mixture of minute fragments of glass.

This syringe, however, can be applied to only the case where a single kind of injection agent is used. Where two or more injections are to be injected, i.e., a mixed solution of two injections A and B is to be injected, these injections A and B must be mixed previously. In this case, even when the injections A and B are solely present, respectively, and also stable for a long-time preservation, the mixture of injections A and B is difficult to maintain its stability.

The solid antibiotic, steroid and other injections described above is dissolved in a solution and the resultant injection liquid is injected. In an emergent medical scene, doing such an operation is very troublesome. Further, the syringe, which includes the needle holder 1 and the cylinder 4 fabricated separately, is fabricated at high production cost. Disposing such a syringe, therefore, is wasteful.

In order to avoid such an inconvenience, the syringe as shown in FIGS. 29(a) and 29(b) which is disclosed in Japanese Preliminary Publication No. sho 60-72561 was proposed. The syringe includes a cylinder 10 having a syringe needle connection portion 11 formed at one end and a plunger insertion hole 12 formed at the other end and a plunger 13 inserted from the hole 12. In the cylinder 10, a swelling portion 17 is formed and a partition portion 14 located apart from the swelling portion 17 divides the cylinder 10 into two chambers 15 and 16. The chamber 15 contains injection powder and the chamber 16 is filled with its solution or diluted solution.

In use, when the plunger 13 is pushed, the pressure in the chamber 16 is increased. As a result, the partition portion 14 moves toward the syringe needle to reach the swelling portion 17 as shown in FIG. 29(b). The swelling portion of the cylinder constitutes a passage 17. When the partition portion 14 reaches this portion, the solution contained in the chamber 16 flows into the chamber 15 through the passage 17. As a result, the powder is solved to provide an injection liquid. Thereafter, air remaining in the chamber 15 is discharged from the syringe needle. The resultant injection is given to a patient.

The syringe disclosed in Japanese Preliminary Publication No. Sho 60-72561 can previously contain two different injections or injection agents. A cap 18, which is only one means of sealing the side of the syringe needle, is likely to come off. Therefore, the sealing is unstable and the preservation of the injection agents for a long time is difficult. In using local anesthetic, many clinical doctors say that the effect of a treatment medicine is more manifest in separate injections than in mixed injections. Specifically, it is preferable to first inject local anesthetic without mixing the local anesthetic with a treatment medicine to lose the sense at the affected part, and thereafter inject the treatment medicine.

SUMMARY OF THE INVENTION

The present invention intends to solve the above problem and provide a syringe which can be manufactured at low cost enough to be disposable, can accommodate one or plural different injection agents, and provide an excellent sealing property making easy the preservation for a long time.

Another object of the present invention is to provide a syringe which permits plural injection agents to be preserved separately, and permits the injection to be done after respective injection agents have been mixed as necessity requires.

Still another object of the present invention is to provide a syringe which permits separate injection of injecting an A agent without mixing plural injection agents and thereafter injecting a B agent, as necessity requires.

In order to attain the above object, the present invention, in a syringe comprising a cylinder having a connection portion for a syringe needle at one end and an opening at the other end, and a plunger to be inserted into the cylinder from the opening, is characterized in that

- between said connection portion and said plunger within said cylinder, at least one partition is slidably provided to divide watertightly the internal space into plural chambers of said cylinder;
- within at least one chamber between said partitions or between said partition and said plunger, an injection agent is accommodated; and
- a passage communicating each of said chambers with said connection portion is provided when said plunger is moved to the side of said syringe needle.

It is preferred that a plurality of partitions are provided so that two or more chambers are formed between said partitions or between said partition and said plunger and said chambers are filled with different injection agents.

Such a configuration may be adopted that said passage is formed between said chambers, and after the injection agents within said chambers are collected into a single chamber as said plunger advances, the resultant injection agent is injected.

Such a configuration may be adopted that said passage is formed on only the side of said connection portion, and as said plunger advances, the injection agents in the respective chambers are sequentially injected without being mixed.

Such a configuration may be adopted that said passage includes an enlarged portion formed in the neighborhood of said syringe needle connection portion, a cylindrical receiver, accommodated in said enlarged portion, for slidably receiving said partition inside itself and a passing-through passage formed in said receiver.

The present invention is characterized by comprising a cylinder having a connection portion for a syringe needle at one end and an opening at the other end; two partitions formed apart from each other within said cylinder; a hole formed in one of said partitions remote from said connection portion; a small cylinder whose tip abuts on said one partition and which rotatably abuts on the inside of said cylinder; a valve member, residing at the tip of said small cylinder, for communicating the chamber between said partitions with a chamber formed in said small cylinder in accord with the hole formed in said partition or separating both chambers from each other in displacement from said hole by rotation of said small cylinder; a plunger slidably provided in said small cylinder; and a passage communicating the chamber between said partitions with said connection portion is provided when said plunger is moved to the side of said syringe needle.

Such a configuration may be adopted that another small cylinder having the same structure as said small cylinder is provided in said cylinder.

Such a configuration may be adopted that said passage includes an enlarged portion formed in the neighborhood of said syringe needle connection portion, a cylindrical receiver, accommodated in said enlarged portion, for slidably receiving said partition inside itself and a passing-through passage formed in said receiver.

Such a configuration may be adopted that a pillar member having a hollow portion communicating with said connection portion and protruding into said cylinder to close its tip is further provided; said passage consists of said hollow portion of said pillar member, a through-hole formed on the side of said pillar member, one of said partitions being slidably fit between the outer periphery of said pillar member and the inner periphery of said cylinder so as to close said through-hole; and said passage is opened when said partition slides toward the side of said syringe needle.

Such a configuration may be adopted that at the center portion of a different partition from said partition, a passage member having a double pipe structure in which an internal cylinder is coaxially held in an external cylinder with a gap from each other is provided, said passage further includes a hollow portion formed in said internal cylinder so that the side of the syringe needle is opened and the side of the plunger is closed and a through-hole formed on the side of said internal cylinder; a small partition for sealing said gap between said internal and external cylinders and closing said through-hole is slidably fit; and said passage is opened when said partition slides toward said small partition.

Such a configuration may be adopted that a passage rod member is provided within said cylinder so as to extend along said cylinder in a longitudinal direction of said cylinder and pass through said partition and said plunger watertightly;

one of said passages includes

- a terminal hollow portion formed along the longitudinal direction of said passage rod member and whose one end communicates with said connection portion, and
- a through-hole formed in the neighborhood of the other end of said terminal hollow portion and communicating said hollow portion with the inside of said cylinder;

the other passage includes at least one intermediate hollow portion separated from said terminal hollow portion and each other and formed along the longitudinal direction of said passage rod member, and

- a through-hole formed in the neighborhood of each of both ends of said intermediate hollow portion and communicating said hollow portion with the inside of said cylinder; and
- as said plunger moves, said partition is shifted from the position where said passage is closed to the position where the it is opened.

Such a configuration may be adopted that said passage consists of at least one pair of through-holes separated from each other by a distance longer than the length of said partition in said cylinder and a pipe connecting the through-holes of each pair with each other.

Such a configuration may be adopted that a passage communicating said pipe with said connection portion is formed at said partition nearest to said syringe needle.

Such configurations may be adopted that the two syringes are arranged in parallel to form a single connection portion for a syringe needle, or otherwise the above two syringes in parallel and a forked connection portion capable of being simultaneously connected to the syringe needle connection portions of said two syringes are provided.

Such a configuration may be adopted that within said cylinder, a hollow fixed type small cylinder is provided coaxially with said cylinder, at a portion of the hollow portion of said fixed type small cylinder a closing portion is formed, and on both sides of said closing portion through-holes are formed to communicate the hollow portion of said fixed type small cylinder with that of said external cylinder;

within said fixed type small cylinder, a partition and a small plunger are fit to form one of said plungers, and between said cylinder and said fixed type small cylinder another partition and a large plunger are fit to form the other chamber;

one of said passages includes a terminal passing-through portion formed within said fixed type small cylinder and one of said through-holes;

the other passage includes the other through-hole; and as said plunger moves, said partition is shifted from the position where said passage is closed to the position where the it is opened.

In the syringe according to the present invention structured as described above, medicine liquids having different properties or solutions are sealed separately from each other in such a manner that they are accommodated in plural chambers in their individual states, and in use, the sealing state is released by an external operation, thereby permitting immediate use. In this case, it is possible to inject the injection liquid after the different injection agents ape mixed with each other, or sequentially inject the accommodated injection agents without being mixed.

Several kinds of problems in actual injection such as bacterial infection, mixture of glass powder and rubber pieces in ampul cutting and vial thrusting and difficulty of sucking high-viscosity medicine can be solved, and plural injection agents can be injected simultaneously by a very simple operation. For this reason, burden for persons engaged in medical treatment and patients can be relaxed.

BRIEF DESCRIPTION OF THE DRAWINGS

FIG. 17(a) and 17(b) are views showing an embodiment of the present invention, (a) being a sectional view of a non-used state and (b) being a sectional view of the state where the operation of injection is carried out;

FIG. 20(a) is a sectional view showing the state where the syringe has started the operation and FIG. 20(b) is a sectional view showing the state where it has completed;

FIG. 21(a) and 21(b) are views showing the structure of another embodiment of the present invention, (a) being a sectional view of a non-used state and (b) being a sectional view of the state where the operation of injection is carried out;

FIG. 22(a) and 22(b) are views showing the structure of still another embodiment of the present invention, (a) being a sectional view of a non-used state and (b) being a sectional view of the state where the operation of injection is carried out;

FIG. 26(a) is a sectional view showing an embodiment in which two syringes are arranged in parallel, and FIG. 26(b) is a syringe needle used in the syringe of FIG. 26(a);

DETAILED DESCRIPTION OF THE PREFERRED EMBODIMENTS

Figure 1:
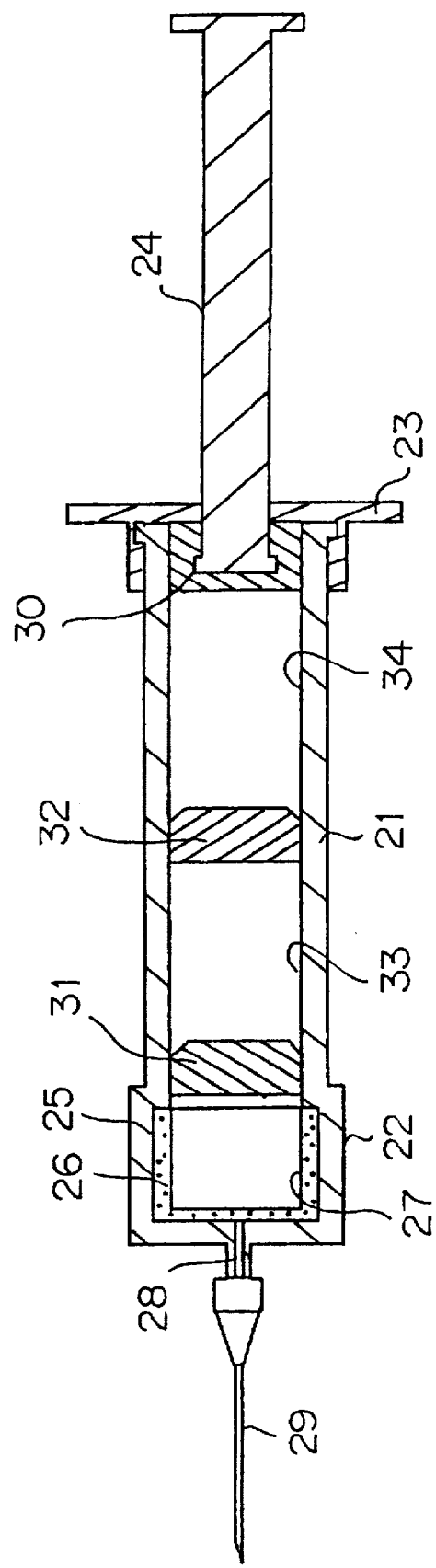
FIG. 1 is a sectional view showing the structure of the syringe according to the present invention.
Figure 2:
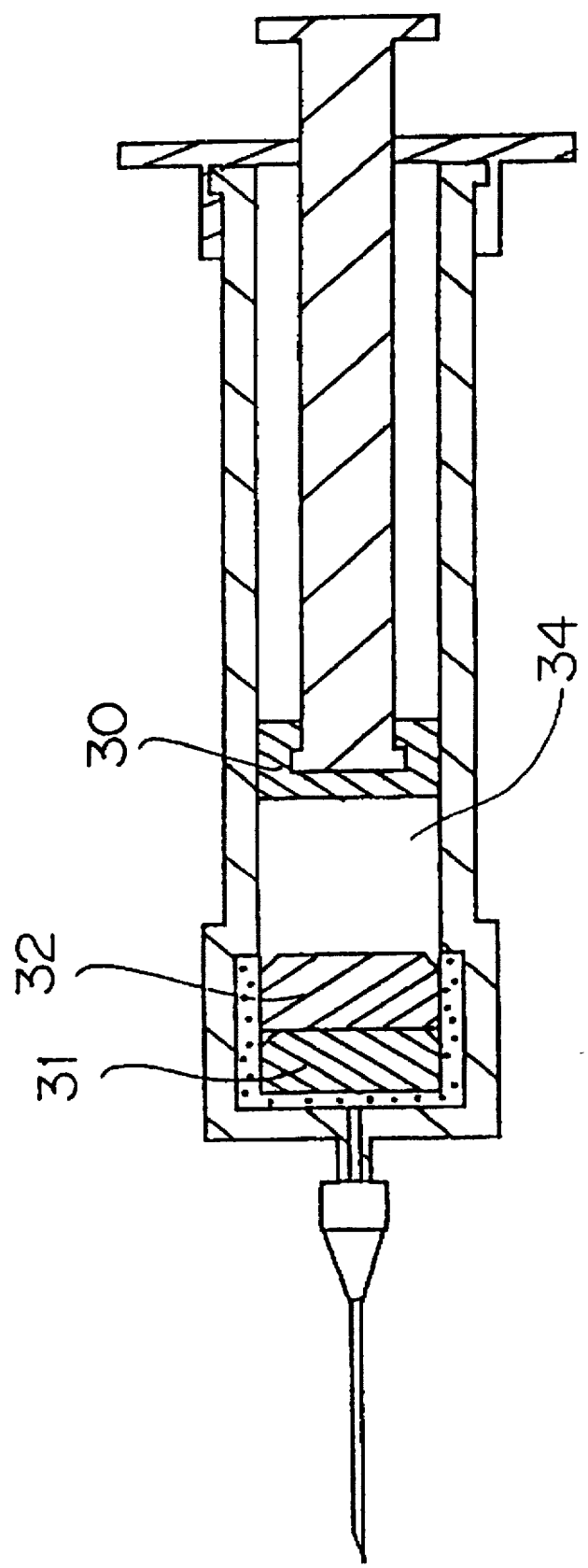
FIG. 2 is a sectional view for explaining the method of using the syringe shown in FIG. 1.

FIGS. 1 and 2 are side sectional views showing an example of an syringe barrel serving as a container containing two kinds of injection liquids or solutions according to the present invention. FIG. 1 shows the state before use and FIG. 2 shows the state in use. In FIGS. 1 and 2, reference numeral 21 denotes a cylinder of glass or synthetic resin; 22 an enlarged-diameter portion provided at the front end of the cylinder 21; 23 a rear end of the cylinder 21; and 24 a plunger. Within the cylinder 21, a chamber 33 sealed by partitions 31 and 32 and a chamber 34 sealed by a partition 32 and a resin stopper 30 are formed. The partitions 31 and 32 are made of flexible resin inclusive of rubber and have appropriate folds formed on the outer periphery. Different injection solutions are sealed in the chambers 33 and 34, respectively. The resin stopper 30 is formed of the same material and in the same structure as in the partition 32. The rear end of the resin stopper 30 is connected to the plunger 24. The enlarged portion 22 is formed at the tip of the partition 31 of the cylinder 21 on the side of the syringe needle. As best seen in the longitudinal cross-sectional view per FIG. 1, in this preferred embodiment the enlarged-diameter portion 22 is formed to be integral with the rest of the body of cylinder 21. A receiver 26 is provided so as to be fit in a recess 25 formed on the inside of the enlarged portion 22. The receiver 26 is a barrel-like body made of porous flexible synthetic resin through which fluid can flow in this example, and the inner periphery forms a chamber 27 having the same diameter as the inner diameter of the cylinder 21. Before the plunger 24 and partitions 31 and 32 are inserted in the cylinder 21, the receiver 26 is bent so as to be inserted into the cylinder 21. The receiver 26 is fit in the enlarged portion so that the receiver 26 is restored to its natural shape. Before use, the chamber 27 whose interior is vacant is communicated with the exterior of the receiver 26 and liquid passage 28. In this state, the chambers 33 and 34 are shut out from the outside. The injection solutions sealed within the chambers 33 and 34, which are not mixed with each other and exposed to the open air, can be preserved for a long time.

In use, when the plunger 24 is advanced to the left side of FIG. 1, both partitions 31 and 32 are also advanced under the liquid pressure. As a result, when the partition 31 is fit in the receiver 26, the solution passage from the chamber 33 to the receiver 26 is formed so that the interior of the chamber 33 is communicated with the syringe needle 29. Then, with the needle 29 directed upward, the plunger 24 is pushed to expel air out of chamber 27. First, the injection within the chamber 33 is led to the solution passage 28 through the receiver 26 in the recess 25 and externally discharged from the needle 29.

When the partition 32 is fit in the receiver 26 as a result of further advance of the plunger 24, a passage communicating the chamber 34 with the receiver 26 is now formed. Then, the injection solution within the chamber 34 is externally discharged. In this way, without mixing the different injection solutions within the chambers 33 and 34, plural injection agents can be sequentially given to a patient by only pushing the plunger 24.

There is a problem of removing air contained in the chamber 34. But, a vacuum filling system which has been developed by Cozzoli Co. Ltd. in U.S.A. Using this system, the chamber 34 can be filled with an injection agent with no air. Thus, taking out air has become unnecessary.

The enlarged portion 22 of the cylinder 21 may be formed as a separate body to be watertightly fit as in the prior art.

Figure 3:
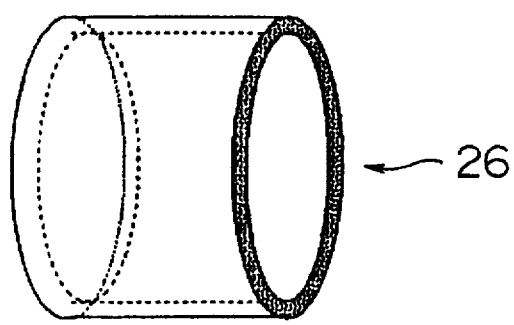
FIGS. 3, 4 and 5 are enlarged perspective views of a receiver used for the syringe shown in FIG. 1.
Figure 4:
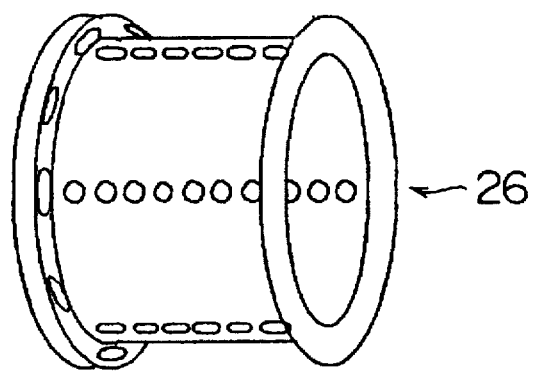
Figure 5:
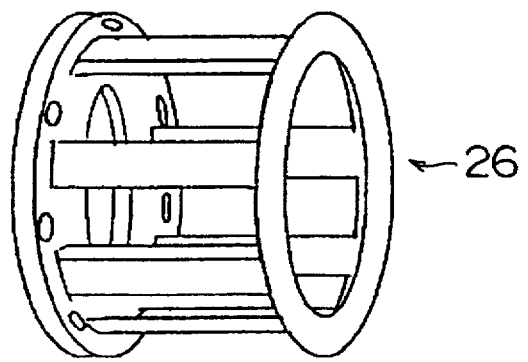

FIG. 3 is a perspective view of an example of the porous receiver 26 used in the above embodiment. The receiver 26 is not limited to such a structure but may be any structure as long as it can receive the partitions and lead the solution to the solution passage 28 through recess 25. For example, as shown in FIGS. 4 and 5, the receiver 26 may be a cylindrical member with openings having the same diameter as that of the cylinder 21 so as to form a space in the recess 25.

Figure 6:
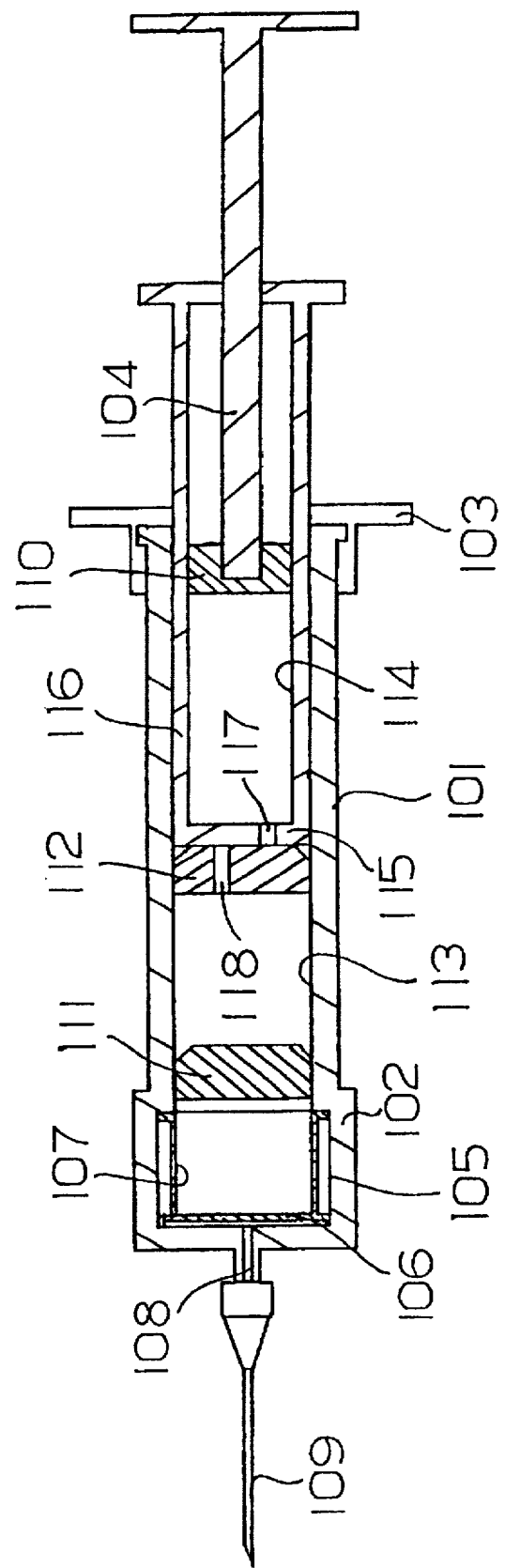
FIG. 6 is a sectional view of an embodiment in which the cylinder is doubly structured.
Figure 7:
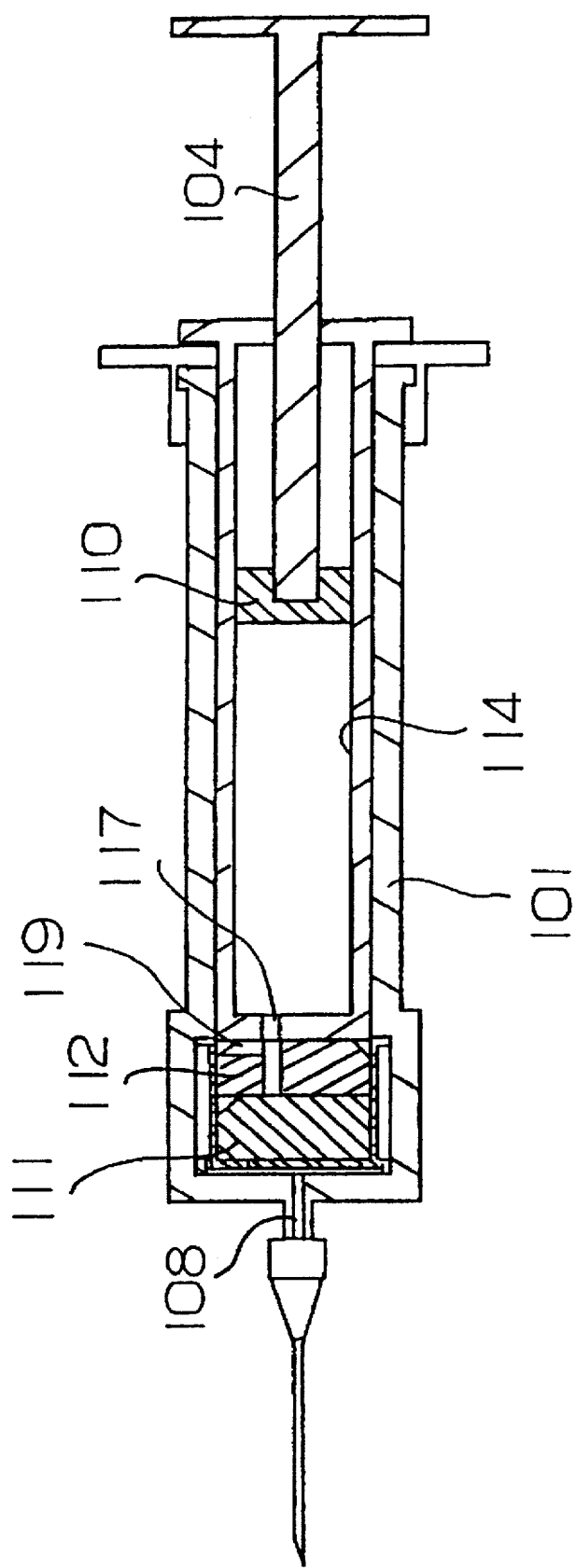
FIG. 7 is a sectional view for explaining the method of using the syringe shown in FIG. 6.
Figure 8:
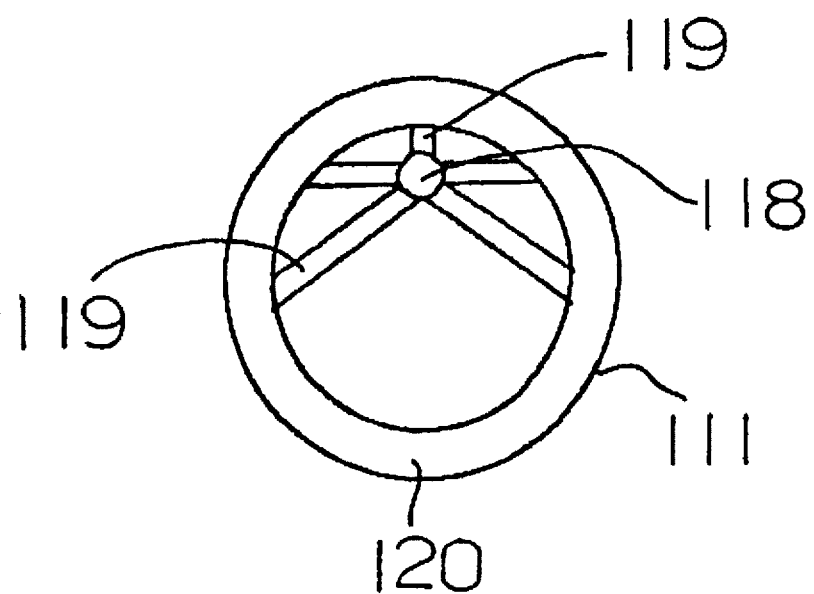
FIG. 8 is a backside view of a typical partition.
Figure 9:
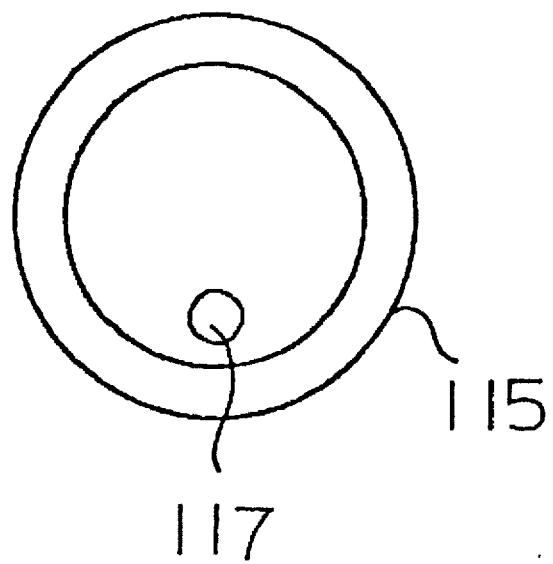
FIG. 9 is a backside view of a typical valve member.

FIGS. 6 and 7 are side sectional views showing an embodiment in which the cylinder is formed in a multiplex manner so as to provide plural injection agent chambers. FIG. 6 shows the state before use and FIG. 7 shows the state in use. This embodiment is also suitable to not only the case where different injection solutions are injected but also the case where a solution is mixed with frozen and dried solid medicines and the injection solution thus created is injected. In this embodiment, a small cylinder 116 which internally abuts on the inside of a cylinder 101 is provided. A valve member 115 is provided at the tip of the small cylinder 116 to form a chamber 114 between itself and a stopper 110. On the front end of the valve member 115, a partition 112 is provided so as to form a chamber 113 between itself and a partition 111. The valve member 115 is provided with an opening 117 and the partition 112 is also provided with an opening 118. When the small cylinder 116 is rotated, the openings 117 and 118 can be aligned with each other so that the chambers 113 and 114 are communicated with each other. An enlarged portion 102 is provided at the needle-side tip of the partition 111 of the cylinder 101. A receiver 106 is provided so as to be fit in the recess 105 provided on the inside of the enlarged portion 102. In this embodiment, the receiver 106 is a barrel-shaped member with pores made of flexible synthetic resin as shown in FIG. 4. The outer periphery of the receiver 106 constitutes a space permitting flow of solution between itself and the recess 105, and the inner periphery forms a chamber 107 having the same diameter as the inner diameter of the cylinder 101. Before use, the interior of the chamber 107 which is vacant is communicated with the outside through the pores of the receiver 106 and the solution passage 108. In this embodiment, where liquids are sealed in both chambers 113 and 114, the syringe can be used in the following manner. When the plunger 104 is advanced, the partition 111 is also advanced as described above. When the partition 111 is fit in the receiver 106, the medicine contained in the chamber 113 is discharged through the pores of the receiver 106 and the solution path. After the medicine contained in the chamber 113 is completely discharged until the partition 112 abuts on the partition 111, the small cylinder 116 is rotated so that the opening 117 of the valve member 115 is aligned with the opening shown in FIG. 8. With the valve member 115 thus opened, when the plunger 104 is further advanced, the medicine contained in the chamber 114 will be discharged externally through the opening 117, grooves 119 of the partition 112 shown in FIG. 8, a recess 120 of the partition 111, pores of the receiver 106, recess 105 and solution passage 108.

The valve member 115 may be opened before the medicine in the chamber 113 is discharged.

Where medicine powder is sealed in the chamber 113 and its solution is sealed in the chamber 114, first, with the valve member opened, the plunger 104 is advanced to lead the liquid in the chamber 114 into the chamber 113. The medicine can be solved sufficiently by shaking. By further advancing the plunger 104, the injection solution can be given to a patient as it is. In this embodiment also, if the syringe is used in such a manner that the openings 117 and 118 are not aligned with each other, the respective injection agents contained in the chambers 113 and 114 can be separately injected.

Figure 10:
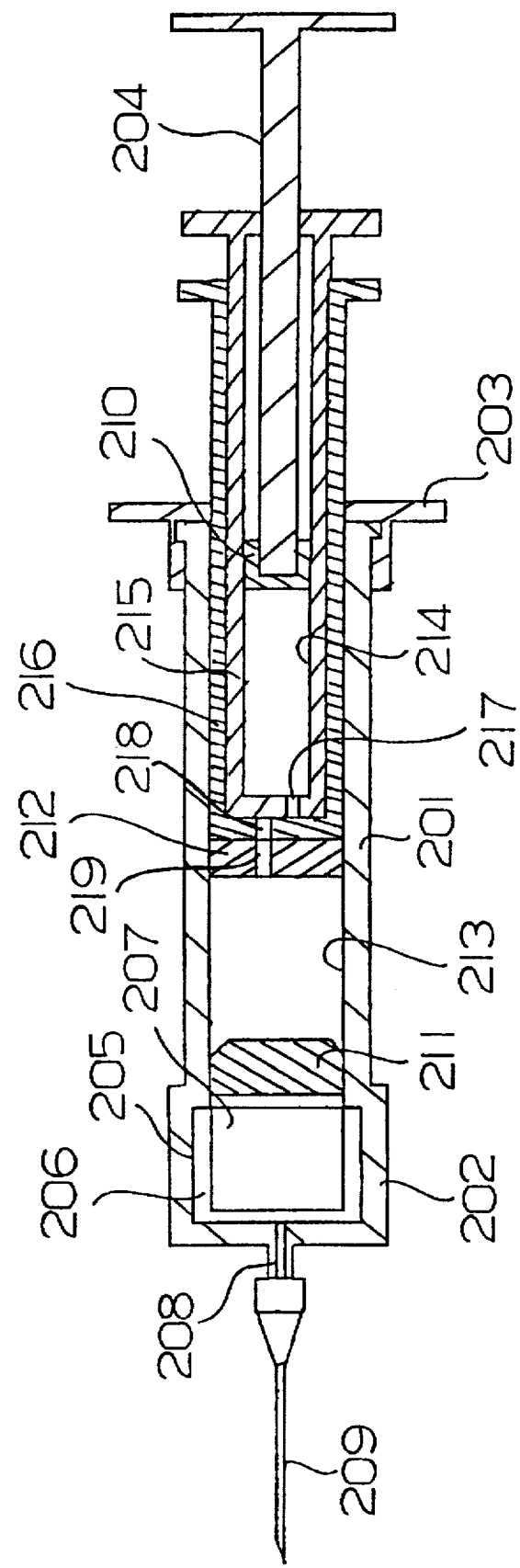
FIG. 10 is a sectional view of an embodiment in which the cylinder according to the present invention is structured in a multiplex manner.

FIG. 10 shows an embodiment similar to the above embodiment but in which the cylinder structure is formed in a triple manner. In this embodiment, in addition to the cylinder 201, cylinders 215 and 216 are provided, and within the cylinder 215, a chamber 214 is formed. An opening 217 is provided at the tip of the cylinder 215, an opening 218 is provided at the tip of the cylinder 216 and an opening 219 is provided at a partition 219 fixed to the tip of the cylinder 216. These openings constitute different valves. In use, when the cylinder 215 is rotated so that the opening 217 and the openings 218, 219 are aligned with each other, the chamber 214 is communicated with the chamber 213. Thus, the injection agent contained in the chamber 214 can be supplied to the chamber 213, or otherwise can be directly discharged as in the embodiment described above. In this case, the partition 211 is preferably provided with grooves as in FIG. 8.

In this embodiment also, if the syringe is used in such a manner that the openings 217, 218 and 219 are not aligned with each other, the respective injection agents contained in the chambers 213 and 214 can be separately injected without being mixed.

The enlarged portion 202, recess 205 formed on its inside, receiver 206 fit in the recess 205 and solution passage 208 may be structured in the same fashion as in the previous embodiment.

Figure 11:
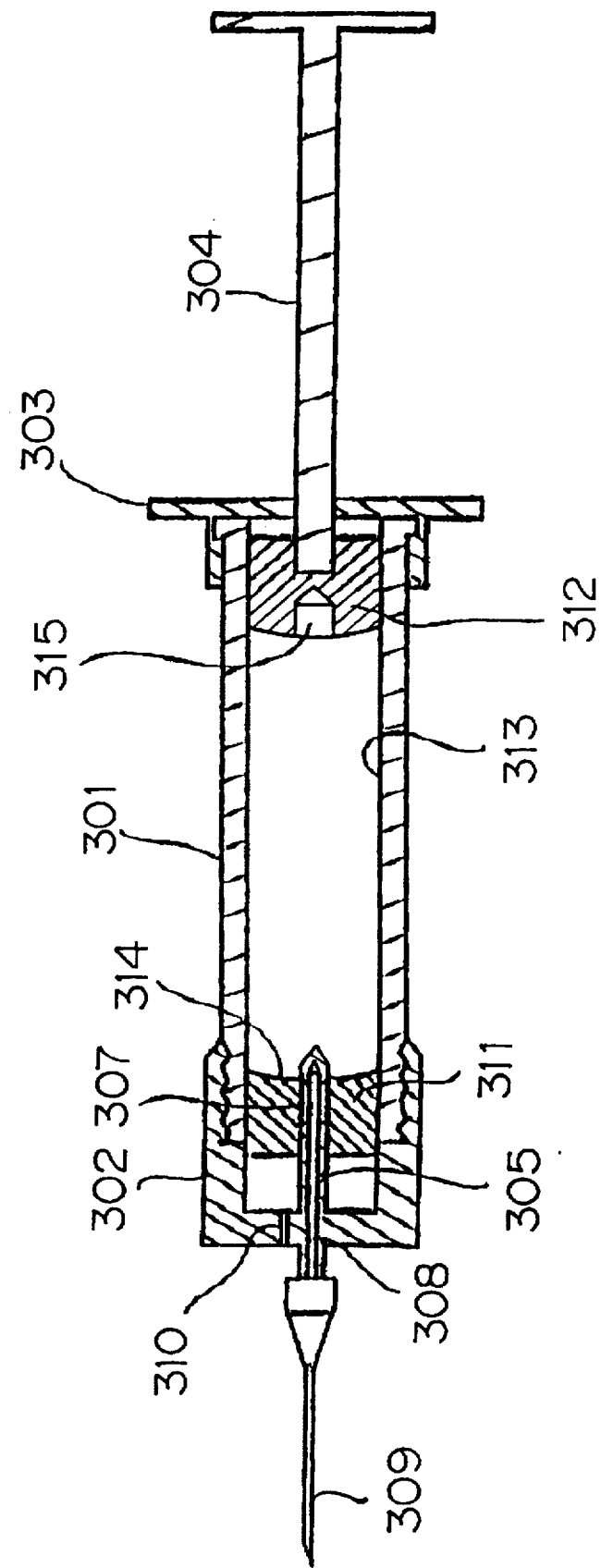
FIG. 11 is a sectional view showing the structure of an embodiment in which a pillar member is used.
Figure 12:
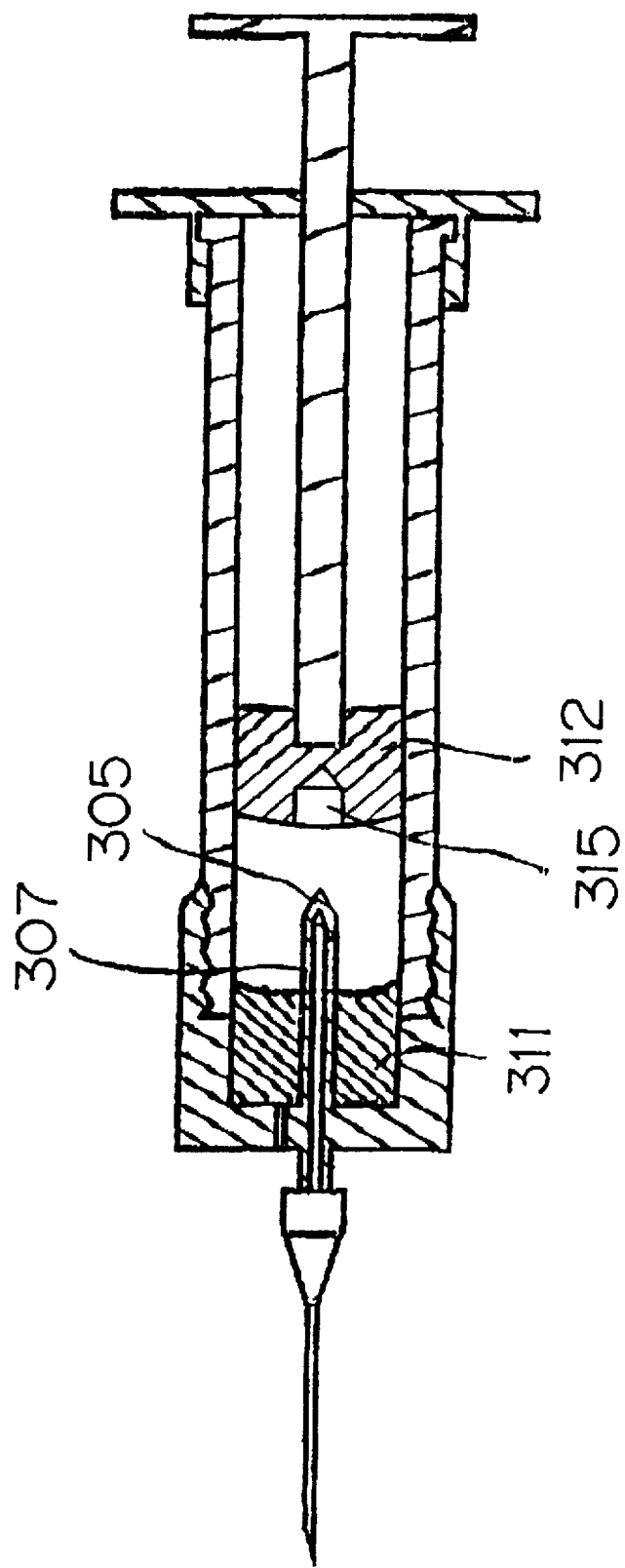
FIG. 12 is a sectional view for explaining the operation of the syringe shown in FIG. 11.

FIGS. 11 and 12 are side sectional views showing still another embodiment. FIG. 11 shows the state before use and FIG. 12 shows the state in use. In FIG. 11, reference numeral 301 denotes a cylinder made of synthetic resin or glass; 302 a tip of the cylinder; 303 a rear end; and 304 a plunger. Within the cylinder 301, a chamber 313 which is watertightly sealed by partitions 311 and 312 of flexible resin is provided. At the center portion of the cylinder tip 302, a cylindrical pillar member 305 which projects into the cylinder 301 and has a sharp tip is provided, and within the pillar member, a solution passage 308 communicating with the side of the syringe needle 309 is passed. The solution passage 308 is communicated with the inside of the cylinder 301 through an opening portion 307 provided in the pillar member 305.

The partition 311 in this embodiment has a doughnut shape having a hole at its center. Before use, the inner periphery of the partition 311 is fit in the outer periphery of the pillar member to close the above opening portion 307 tightly, and the outer periphery 311 of the partition intimately abuts on the inner periphery of the cylinder 301 to stop communication with the outside. The tip of the pillar member 305 is made sharp so that it can be easily inserted into the central opening of the partition 312. The partition 312 is made of the same flexible synthetic resin as that of the partition 311, and its syringe needle side has such a shape that the sharp tip of the pillar member 305 can be inserted with no opening. The outer periphery of the partition 312 intimately abuts on the inner wall of the cylinder 301 to stop communication with the open air. Thus, the chamber 313 formed between the partitions 311 and 312 is completely shut out from the open air. An injection solution is sealed in the chamber 313. Although the tip portion 302 shown in FIG. 11 is a separate body from the cylinder 301, which is watertightly fit, it may be formed integrally to the cylinder 301.

In use, when the plunger 304 is advanced to the left side of FIG. 11, the partition 312 is advanced and the partition 311 is also advanced under the liquid pressure created. An air opening 310 serves to release the air pressure generated by advancement of the partition 311. When the partition 311 continues to advance, the opening portion 307 of the pillar member is opened for the chamber 313 so that the chamber 313 is communicated with the open air through the opening portion 307, solution passage 308 and syringe needle 309. In this state, when the cylinder is directed upward, air bubbles in the chamber 313 are led to the opening portion through the depression provided at the partition 311. When the plunger 304 is further pushed, the air bubbles are discharged externally through the syringe needle 309. In this state, an injection can be immediately given to a patient. As shown in FIG. 12, when the plunger 304 is pushed, the injection solution within the chamber 313 is led to the solution passage 308 and externally discharged from the syringe needle 309. When the plunger 304 continues to advance, the tip of the pillar member 305 is fit into the concave portion and the injection solution in the chamber 313 is discharged almost completely. Thus, the plunger 304 has only to be pushed in order to give automatically the injection solution contained within the chamber 313 to a patient.

Figure 13:
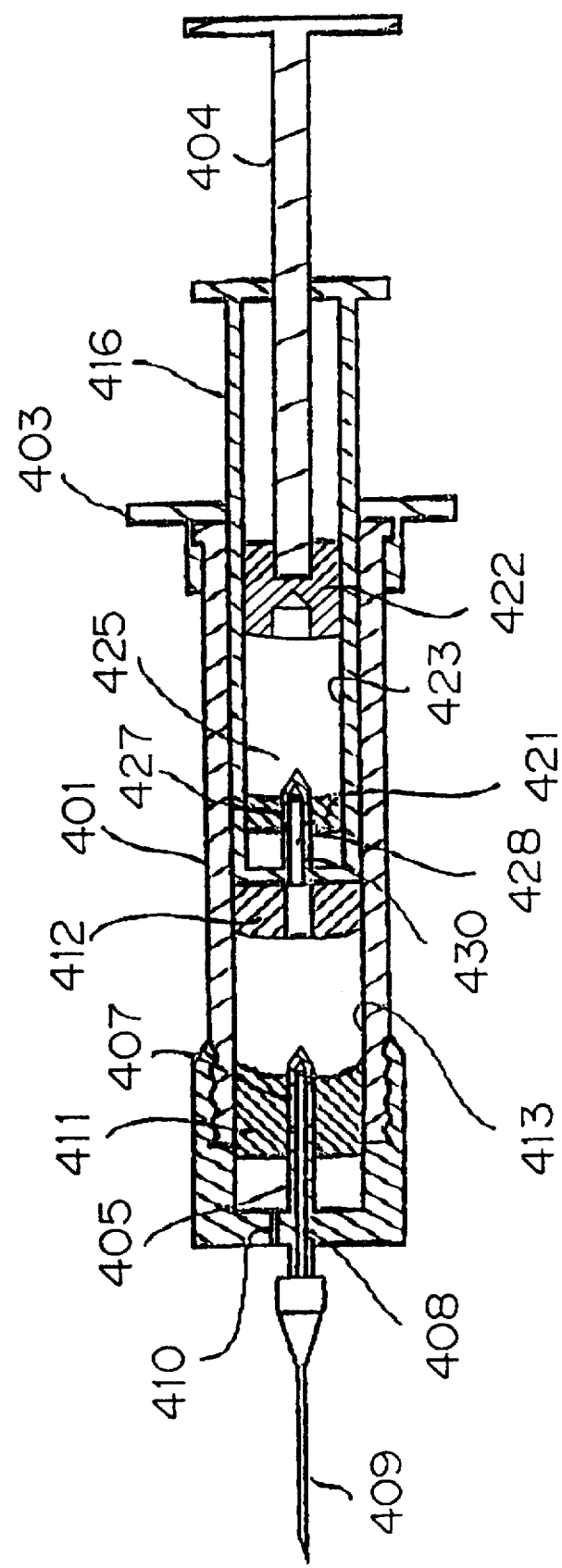
FIG. 13 is a sectional view of an embodiment in which the cylinder of the syringe shown in FIG. 11 is doubly structured.

FIG. 13 is a side sectional views showing an embodiment in which the cylinder is formed in a multiplex manner so as to provide plural injection agent chambers. This embodiment is also suitable to not only the case where different injection solutions are injected but also the case where a solution is mixed with frozen and dried solid medicines and the injection solution thus created is injected. In this embodiment, a small cylinder 416 which internally abuts on the inside of a cylinder 401 is provided. A partition 412 is provided at the tip of the cylinder 401 so as to form a chamber 413 between itself and a partition 411. Further, within the cylinder 416, a chamber 423 is formed between the partition 422 and partition 421. Different medicines are sealed in the chambers 413 and 423.

In this embodiment, where liquids are sealed in both chambers 413 and 423, the syringe can be used in the following manner. When the plunger 404 is advanced, the partition 421 is also advanced as described above. Then, an opening portion 427 provided at a pillar member 425 opens so that the chamber 423 and the chamber 413 are communicated with each other through a solution passage 428. Reference numeral 430 denotes an opening for communicating the pillar member with the solution passage so that the partition 421 is not prevented from advancing. When the plunger 404 is further advanced or otherwise the cylinder 416 is advanced, the partition 411 is advanced under liquid pressure created. Thus, the passage 407 provided at the pillar member 405 is opened so that the medicine contained in the chamber 413 can be externally discharged through the solution passage 408. By further advancing the plunger 404 and the cylinder 416 as they are, the injection solutions contained in the chambers 413 and 423 can be given to a patient.

In FIG. 13, where frozen dried medicine powder is sealed in the chamber 413 and its solution is sealed in the chamber 423, first, with the valve member opened, the plunger 404 is advanced to lead the solution in the chamber 423 into the chamber 413 in the same manner as described above. The solid medicine contained within the chamber 413 is solved sufficiently. Thereafter, by further advancing the plunger 404 and the cylinder 416, the injection solution can be immediately given to a patient.

Figure 14:
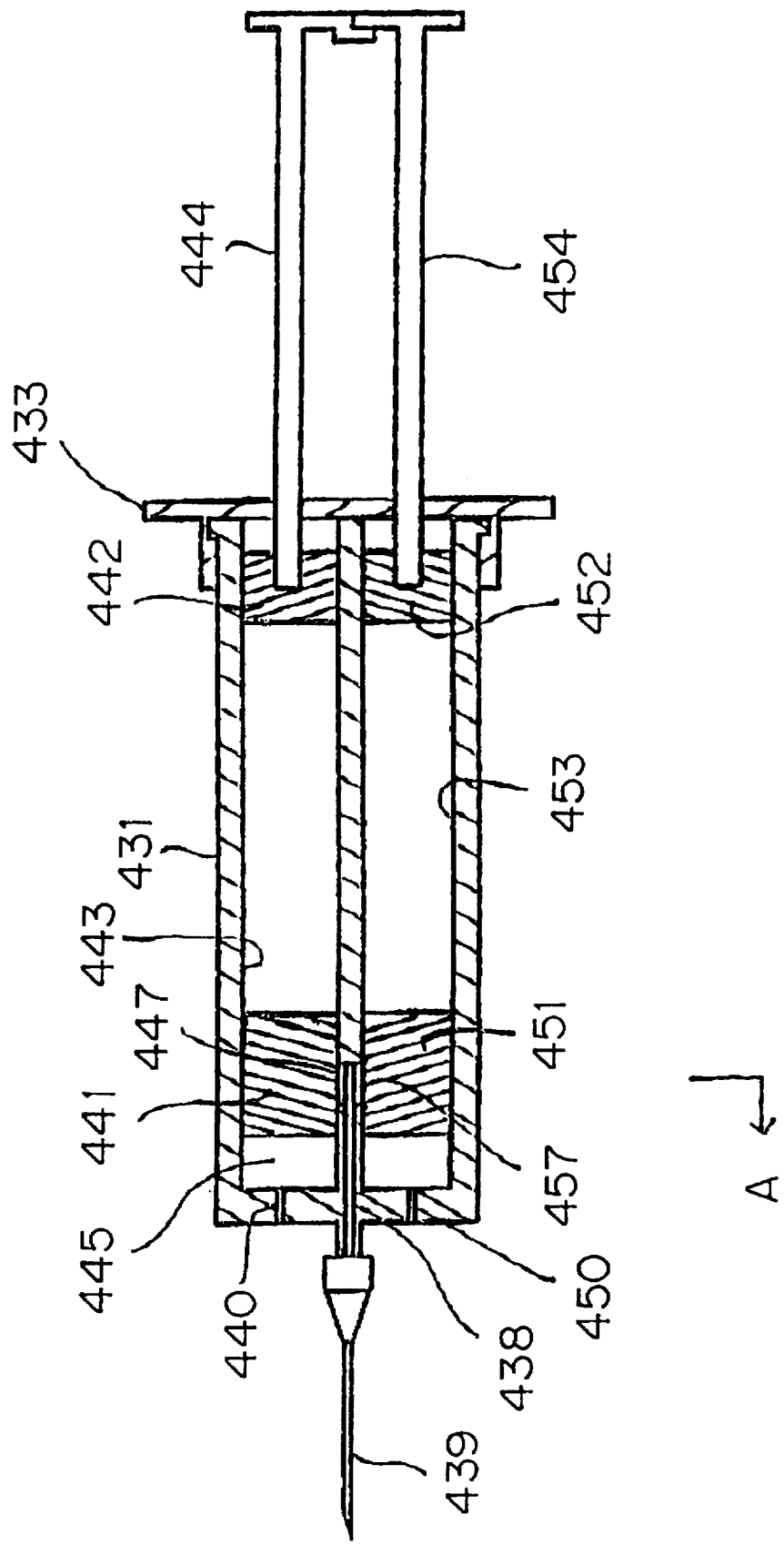
FIG. 14 is a sectional view of an embodiment in which two chambers are arranged in parallel in a single cylinder.
Figure 15:
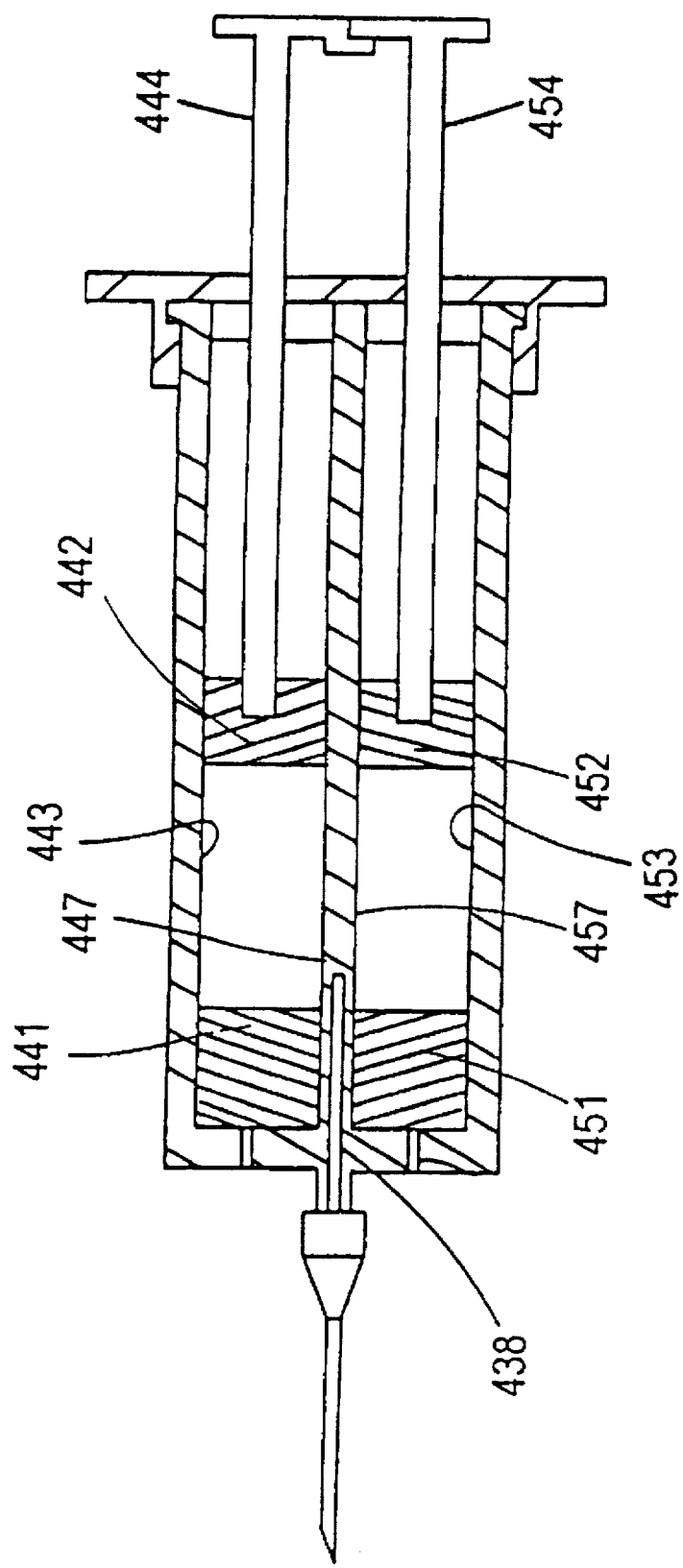
FIG. 15 is a side sectional view of the state where the embodiment shown in FIG. 14 is in use.
Figure 16:
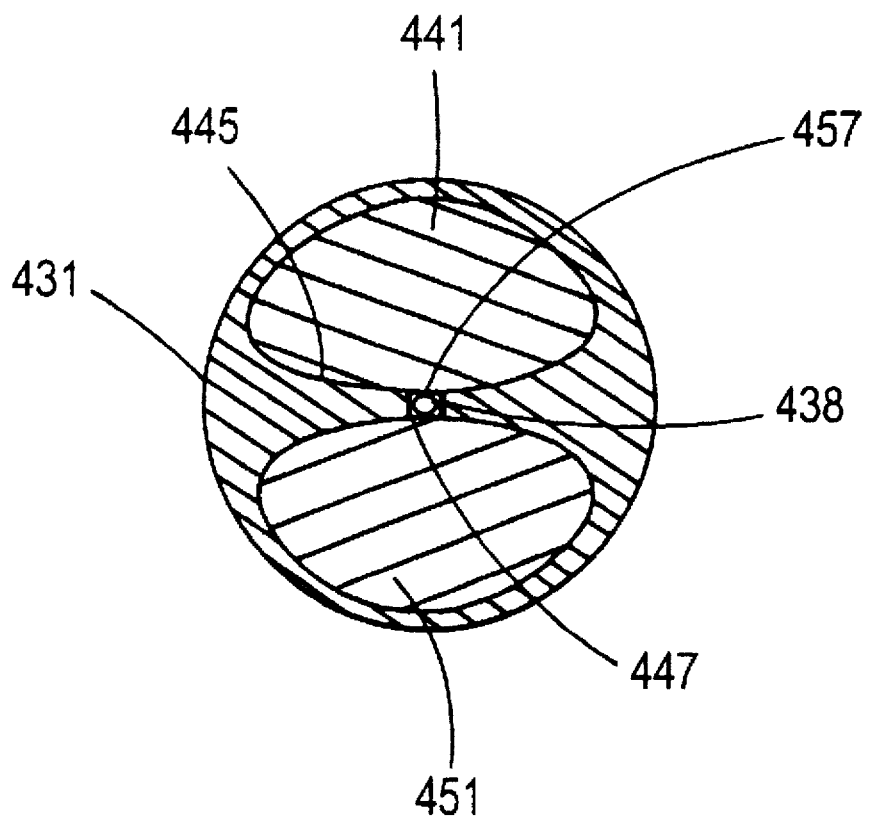
FIG. 16 is an front sectional view of the neighborhood of the opening portion 447 in the embodiment shown in FIG. 15.

FIGS. 14 and 15 are side sectional views of an embodiment in which chambers with different injections sealed are arranged in parallel within the cylinder. FIG. 16 is a side sectional view of the neighborhood of the partition 441 taken along line A—A. In this embodiment, the interior of the cylinder 431 is partitioned longitudinally in two columns to provide a chamber 443 watertightly sealed by partitions 441 and 442 and a chamber 453 watertightly sealed by partitions 451 and 452. At the front end of a partition plate 445 partitioning the both chambers on the side of the syringe needle, a solution passage 438 communicating with the open air is provided which is communicated with the chamber 443 through an opening portion 447 and with the chamber 453 through the opening portion 457.

In use, as shown in FIG. 15, when plungers 444 and 454 are advanced simultaneously or separately, the partitions 441 and 451 are also advanced simultaneously or separately. Then, the opening portions 447 and 457 are opened. As a result, the medicine contained in the chamber 443 can be externally discharged through the opening portion 447 and solution passage 438 while the medicine contained in the chamber 453 can be externally discharged through the opening portion 457 and solution passage 438.

The cylinder 521 of a syringe 520 as shown in FIGS. 17(a) and 17(b), which can be manufactured by molding of glass and plastic and has a cylindrical shape, is provided with a connection portion 521a for a syringe needle 522 at one end and an opening 521b and a flange 521c at the other end.

Within the cylinder 521, a rod-like member 523 having a hollow portion 523a communicating with the connection portion 521a is located, and its tip on the side of a plunger is closed. On the side of the rod member, a through-hole 523b is made. The rod-like member 523 can formed integrally to the cylinder 521.

A partition 524 is fit watertightly and slidably owing to its elasticity of material between the external surface of the rod-like member 523 and the internal surface of the cylinder 521. A plunger 525, which is made of the same elastic material as that of the partition, includes a female screw formed on the opening side at the center. The female screw is screwed to a male screw at the tip of a haft of the plunger.

Within the cylinder 521, the partition 524 forms two chambers 526 and 527. Only the chamber 526 sandwiched between the partition and plunger is filled with an injection solution. The other chamber 527 is left vacant. In the wall on the side of the syringe needle, an air vent 521d is formed. Because of such a structure, the syringe according to this embodiment can be easily manufactured at low cost.

An explanation will be given of the operation of the syringe.

First, with the syringe needle directed upwards, as shown in FIG. 17(b), the plunger 525 is pushed toward the syringe needle 522. This enhances the pressure of the chamber 526. The partition 524 moves toward the syringe needle 522 letting air out of the chamber 527 through the vent 521d, thereby opening the through-hole 523. Where the chamber 526 contains air, when the plunger 525 is pushed as it is, air passes through the through-hole 523b and the hollow portion 523a and is taken out from the syringe 522. After air is taken out, an injection is given to a patient.

Figure 18:
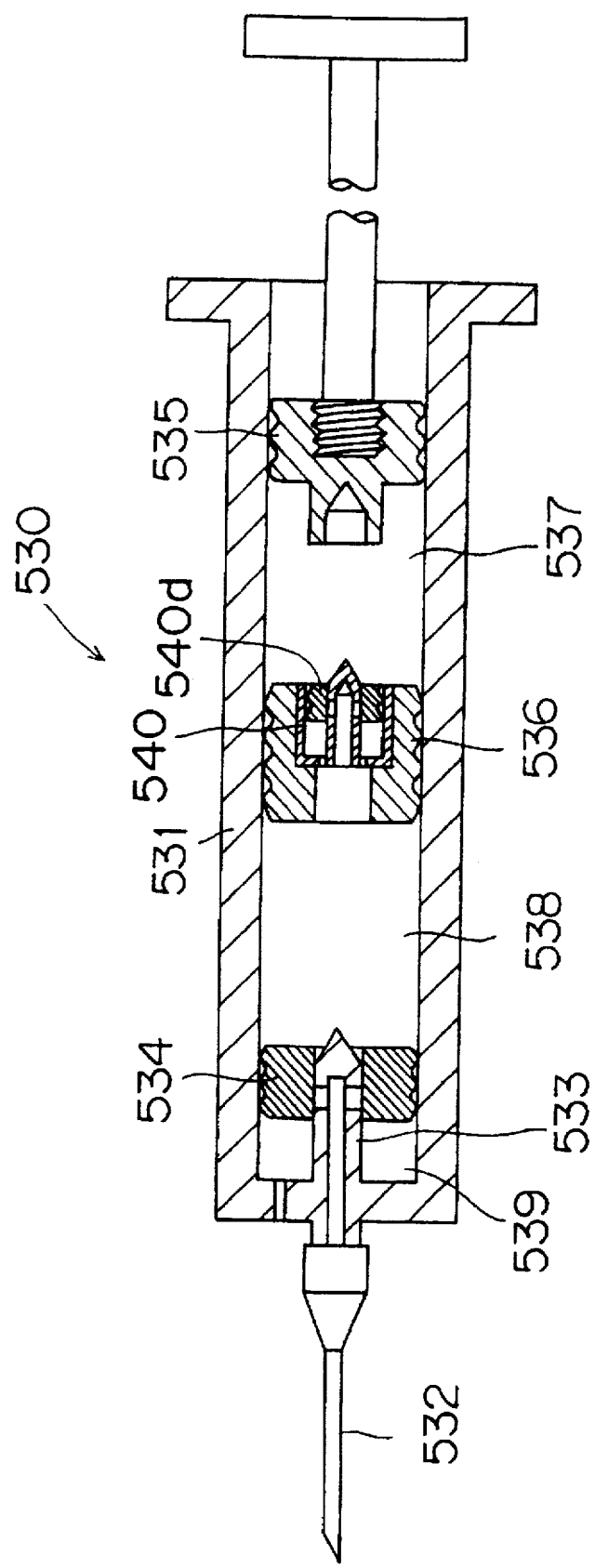
FIG. 18 is a sectional view showing the structure of another embodiment of the present invention.

FIGS. 18 to 20 show syringes which can previously accommodate two different injection solutions and preserve them for a long time. In FIG. 18, a syringe 530 includes a cylinder 531, a syringe needle 532, a rod-like member 533, a partition 534 and a plunger 535 which have the same configuration as in the embodiment shown in FIG. 17.

This embodiment is characterized in that another partition 531 is formed between the partition 534 and the plunger 535. Thus, there are three chambers 537, 538 and 539. Of these chambers, the chamber 538 formed between the partitions 534 and 536 and the chamber 537 formed between the partition 538 and the plunger 535 are filled with different injection agents. The partition 536 has an opening formed centrally in which a passage member 540 is watertightly fit.

Figure 19B:
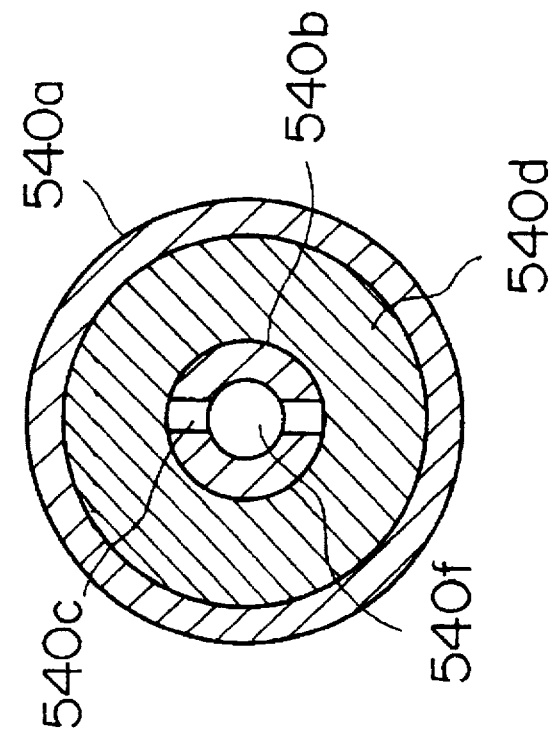
FIGS. 19(a) and 19(b) are views showing the details of a passage member used in the embodiment of FIG. 18, (a) being a sectional view thereof and (b) being a sectional view along line I—I of (a)
Figure 19A:
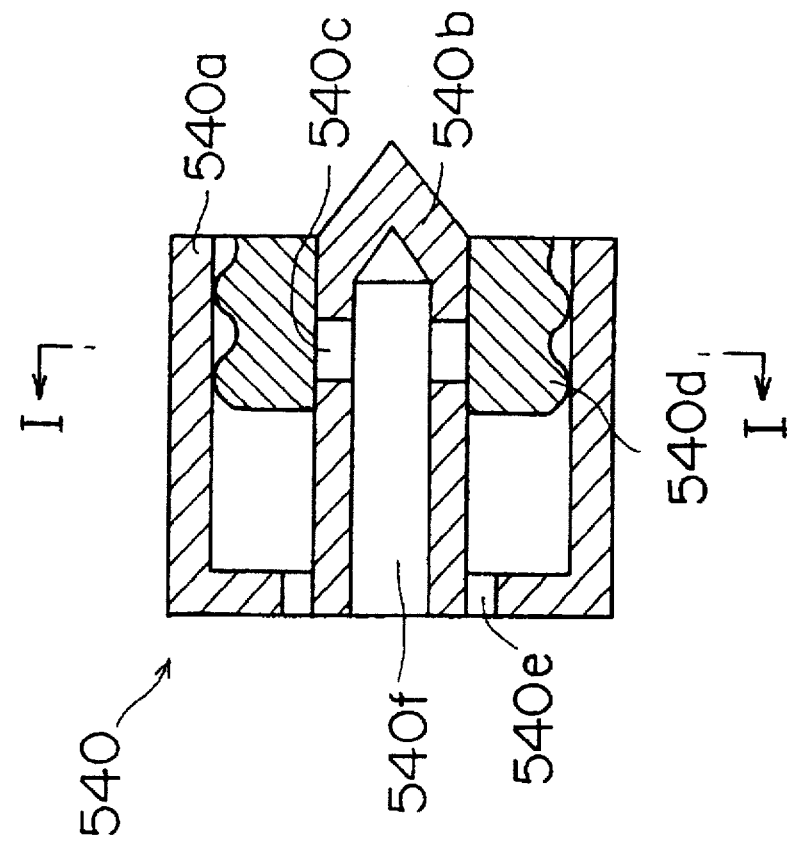
Figure 23:
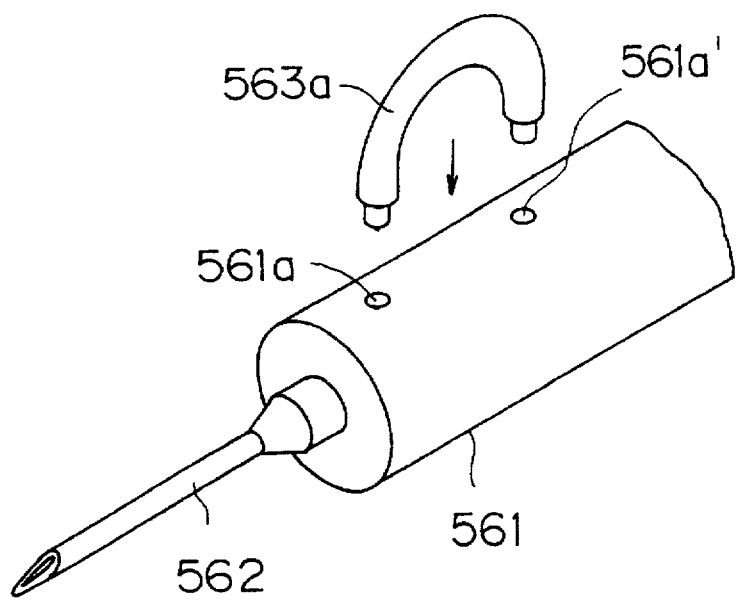
FIG. 23 is a partial perspective view of the embodiment of embodiment of FIG. 22.

FIGS. 19(a) and 19(b) show the details of the above passage member 540. As seen from the figures, the passage member 540 includes an outer cylinder 540a and an inner cylinder 540b which are arranged concentrically. The outer cylinder 540a is coupled with the end of the inner cylinder 540b at the end on its needle side. The inner cylinder 540b has a hollow portion 540f with the needle side being opened and the plunger side being closed and having a sharp tip, through the side of which a through-hole 540c vertically passes. Between the external cylinder 540a and the internal cylinder 540b, a small partition 540d made of the same elastic material as those of the partitions 534 and 536 is watertightly fit. Numeral 540e denotes an air vent. The passage member 540 having such a configuration is fit in the partition 538 so that the chambers 537 and 538 can be maintained in a watertightly divided state.

Now referring to FIGS. 20(a) and 20(b), an explanation will be given of the operation of the syringe shown in FIG. 18.

First, with the needle 532 of the syringe 530 directed upwards, the plunger 525 is pushed toward the syringe needle 532. This enhances the pressure of the chamber 537.

Then, the small partition 540d moves toward the side of the syringe needle 532 to open the through-hole 540c. Thus, the passages 540 and 540f communicating the chamber 537 with the chamber 538 are opened. The air contained in the chamber 537 is first supplied into the chamber 538 and subsequently the injection agent also starts to be supplied.

Thus, the pressure in the chamber 538 is also enhanced so that the partition 534 moves toward the syringe needle 532. As a result, the through-hole 533b opens so that the passages 533a and 533b between the chamber 538 and the connection portion 531a are communicated with each other.

Where air as well as the injection solution is contained in the chamber 538, the air in the chamber 538 is exhausted from the opened passages. As a result, air contained in the chambers 537 and 538 can be completely taken out. After the air is taken out, with the chambers 537 and 538 filled with the injection solution, an injection is given to a patient.

FIG. 20(b) shows the state of the syringe after the injection is completed. In order that the injection contained in the syringe is completely discharged, a concave portion 536a receiving the rod-like member 533 is formed in the partition 536, and a protrusion 535a (FIG. 20(a)) complementary to the small partition 540d is formed.

Where the injection agent in the chamber 538 is solid such as powder, the air in the chamber 537 is exhausted and the liquid in the chamber 537 is subsequently supplied into the chamber 538. This can be performed by previously adjusting the amount of air. When the liquid is completely supplied into the chamber 538, the syringe is shaken to solve the injection powder into a solution. Thereafter, with the air in the chamber 538 exhausted, an injection will be given to a patient.

The cylinder 551 of the syringe 550 as shown in FIGS. 21(a) and 21(b) has also substantially the same structure as those of the cylinders 521 and 531 in the first and second embodiments, but is different in a passage rod member 553 provided on the center axis within the cylinder instead of the rod-like member. The passage rod member 553, which is a slender rod having an outer disk-shape, is extended from the end on the side of a connection portion 551a for a syringe needle to an opening end 551b on the opposite side to pass through the partitions 554, 556 and plunger 555. The cylinder is partitioned into the chambers 557, 558 and 559 by the partitions and plunger. The chambers 557 and 558 of these chambers are filled with different injection agents.

At the end of the passage rod member 553 on the side of the connection portion 551a, a terminal hollow portion 553a communicating with the syringe needle 552 is formed, and at the end of the terminal hollow portion 553b on the side of the plunger, a through-hole 553b communicating with the chamber 559 is formed. An intermediate hollow portion 553c is formed apart from the terminal hollow portion 553a by a distance longer than the length of the partition 553a. At both ends of the intermediate hollow portion 553c, through-holes 553d and 553e communicating with the inside of the cylinder are formed.

An explanation will be given of the operation of the syringe shown in FIG. 21. As shown in FIG. 21(b), when the plunger 555 is pushed into the cylinder, the pressure in the chamber 557 is enhanced so that the partition member 556 moves toward the syringe needle 556. Thus, the through-hole 553e of the intermediate hollow portion 553c is opened so that the passage consisting of the through-hole 553e, intermediate hollow portion and through-hole 553d is opened. As a result, air and/or injection agent in the chamber 557 moves into the chamber 558 to enhance the pressure in the chamber 558. When the pressure in the chamber 558 is enhanced, the partition 554 moves to open the through-hole 553b. Thus, the air or injection agent is discharged form the syringe needle 552 through the terminal hollow portion 553a.

If the volumes of the injection agent and air in the chamber 558 are suitably set in relation to the volume in the chamber 557, the partition 554 can be shifted toward the syringe needle 552 after the injection agent is completely shifted into the chamber 558. Namely, the chamber 558 can be previously filled with a powder injection agent.

FIGS. 22 to 25 show syringes suitable to inject a very small amount of injection agent such as several kinds of prophylactic vaccine.

Traditionally, such an injection has been carried out in schools or the like. In this case, a school doctor and others prepare an injection solution by mixing injection powder and a solution (or diluted solution), and put the injection solution in a large syringe, and give many persons the prepared injection solution using this single syringe. In this case, it was very problematic to use the single syringe for plural persons and also was difficult to give a single person a fixed amount of injection agent. This embodiment intends to solve such a problem.

The syringe as shown in FIG. 22 has a slender cylinder 561 for injection of a small amount of injection agent. As seen from FIG. 23, the cylinder 561 is provided with plural pairs of through-holes 561a and 561a'; 561b and 561b'; 561c and 561c'; and 561d and 561d'. The pairs of through-holes are coupled with each other by hollow pipes 563a, 563b, 563c and 563d, respectively. The distance between the through-holes of the respective pairs is made longer than the axial length of each of the partitions 564 and 566.

Partitions 564 and 566 and a plunger 561 are fit in the cylinder 561 to form three chambers 567, 568 and 569. The partitions, which may be made of an elastic material as in the previous embodiments, may be formed of a rod of a hard plastic or stainless steel because the internal diameter of the cylinder is small. The chamber 568 between the partitions and chamber 567 between the partition 566 and the plunger 565 are filled with injection agents. The plunger 565 is connected to a grip 570 through a screw.

An explanation will be given of the operation of the syringe according to this embodiment. When the plunger 565 connected to the grip 570 is pushed into the cylinder 561, the pressure in the chamber 567 is enhanced so that the partition 566 moves towards the side of the syringe needle 562. When the partition 566 is positioned between the pair of through-holes 561c and 561c' and between the pair of through-holes 561d and 561d' which are formed on the side nearest to the plunger, the chambers 567 and 568 are communicated with each other through the pipes 563c and 563d. Then, air and an injection agent flow from the chamber 567 into the chamber 568. Thus, the pressure in the chamber 568 is enhanced and the partition 564 is pushed. When the partition 564 is located between the pair of through-holes 561a and 561a' formed on the side of the syringe needle, the chambers 568 and 569 are communicated with each other. Since the chamber 569 and the syringe needle are previously communicated with other, the chamber 568 is eventually communicated with the syringe needle. This embodiment, which is simple in structure, can be also applied to a small-sized cylinder having a small bore size. The syringe according to this embodiment, which can be easily machined by only making through-holes on the side of the cylinder and connecting these through-holes by pipes, can be manufactured at low cost. The syringe according to this embodiment, which is particularly suitable to a small-sized syringe, can be also applied to a syringe having a usual size.

Figure 24:
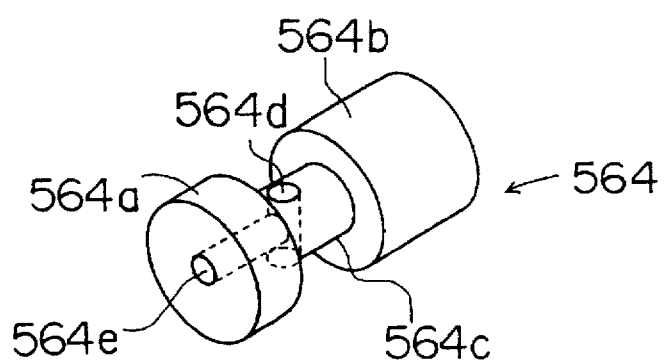
FIG. 24 is a perspective view of a partition.

FIG. 24 is a perspective view of the partition 564 nearest to the side of the syringe needle 562. As seen from FIG. 24, the partition 564 includes front and rear cylinder portions 564a and 564b having equal diameters and a small diameter portion 564c sandwiched between these front and rear cylinder portions. A hole 564d formed vertically to the axis in the small diameter portion 564c is made orthogonal to a hole 564e made along the axis from the end of the one cylinder 564a. As seen from FIG. 22(b), when the partition 564 is brought into contact with the side of the syringe needle of the cylinder 561, the small diameter portion 564c is caused to correspond to the through-holes 561a and 561b so that the passage is not closed.

Figure 25:
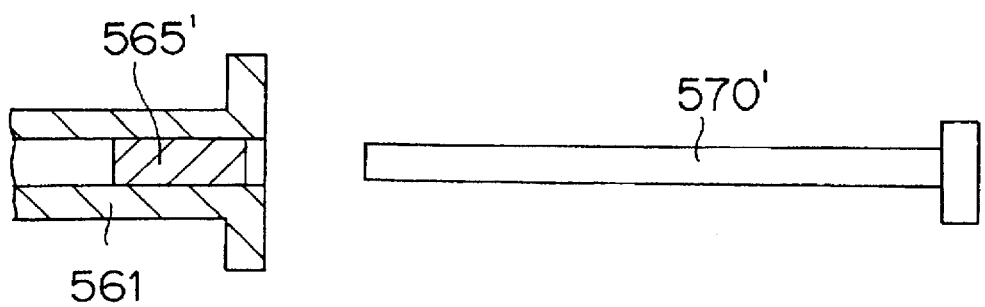
FIG. 25 is a view showing the structure of another plunger in the embodiment of FIG. 22.

FIG. 25 shows another embodiment of a plunger 565' and a grip 570' As seen from FIG. 25, when the plunger 565' is fit in the cylinder 561 so as to be recessed, the plunger 565' with no screw can be also pushed into the cylinder 561.

FIG. 26 shows an embodiment in which two syringes each shown in FIG. 17 arranged in parallel are coupled with each other by coupling members 581 and 582. The cylinders 521 and 521' are previously filled with different injection agents. A syringe needle 583 has a forked connection portion as seen from FIG. 26(b). While the syringe needle is not used, the connection portion of the syringe remains covered with a cap 584. The syringe needle is preferably sealed in a sterilized seal 585.

In use, both plungers, coupled with each other by a coupling tool 586, may be pushed simultaneously, or otherwise individually. The syringe according to this embodiment is suitable to the case where it is not required fop the two injection agents to be combined with each other.

Figures 27A, 27B:
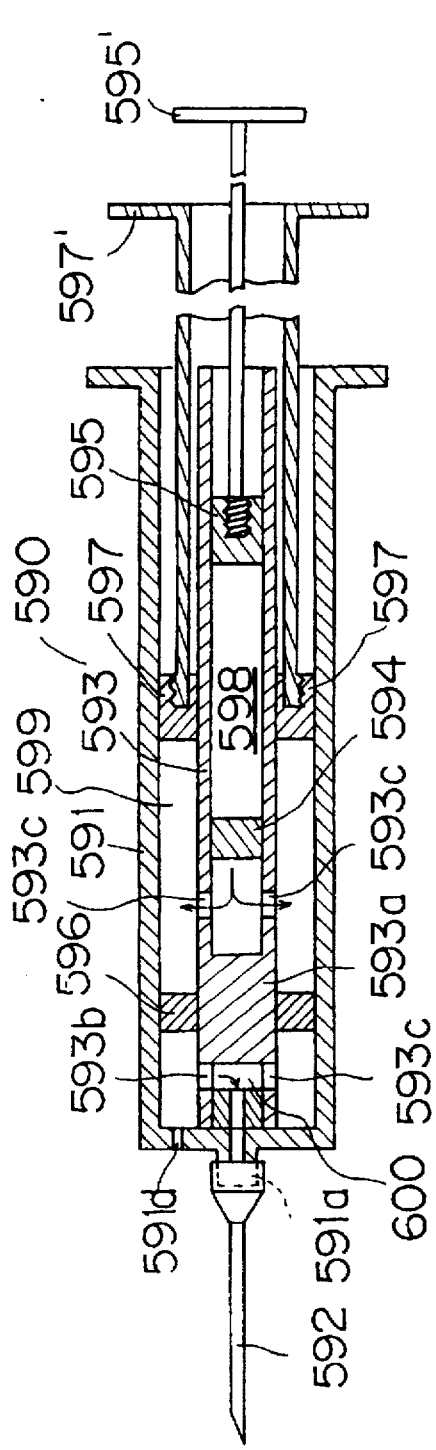
FIGS. 27(a) and 27(b) are views showing a further embodiment of the present invention, (a) being a sectional view and (b) being a perspective view.
Figure 28A:
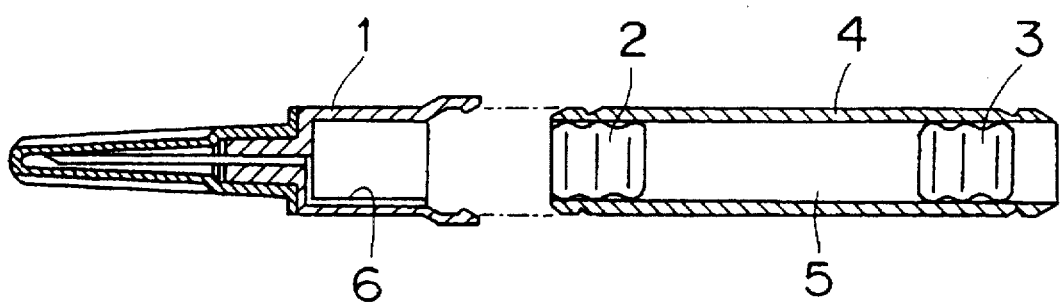
FIGS. 28(a) and 28(b) are sectional views of the syringe according to a prior art.
Figure 28B:
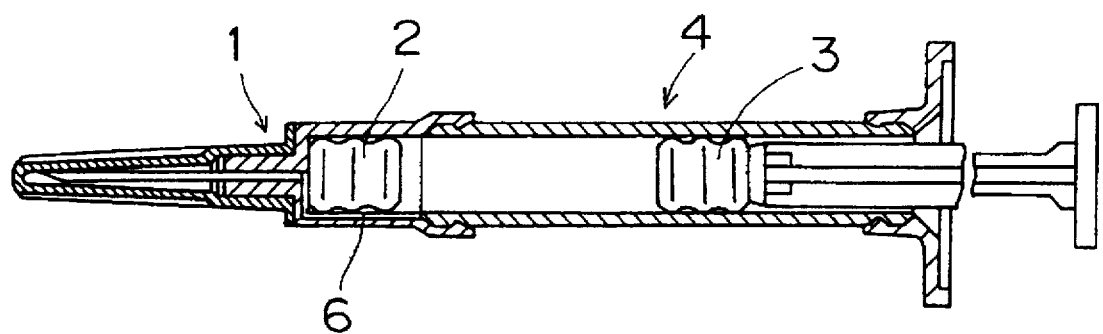
Figure 29A:
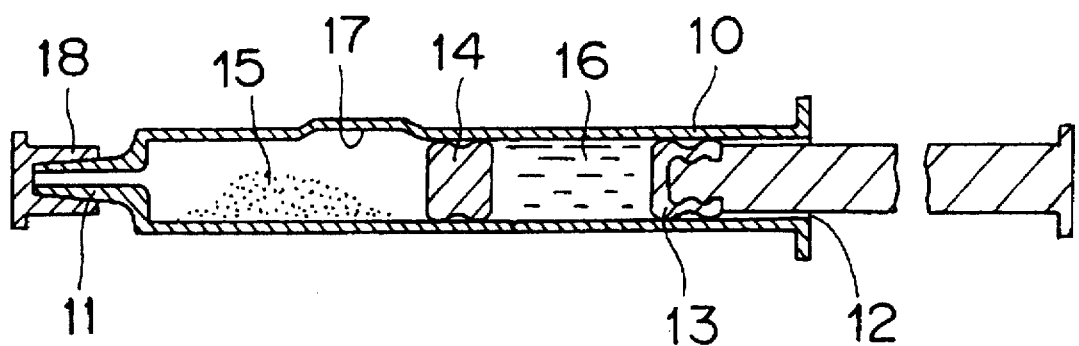
FIGS. 29(a) and 29(b) are sectional views showing the syringe according to another prior art.
Figure 29B:
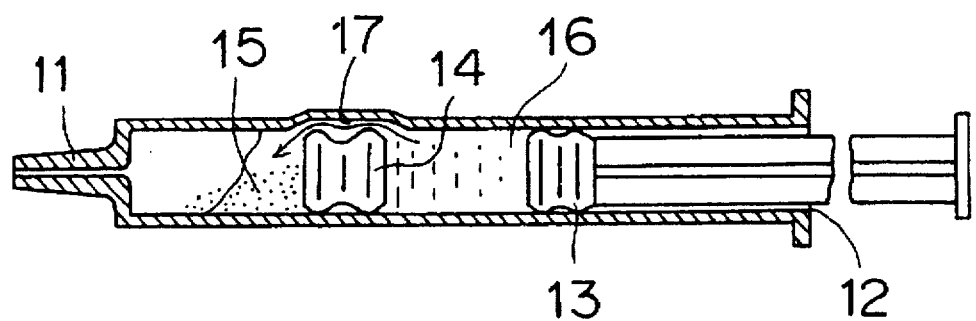

In the embodiment shown in FIG. 27, within a cylinder 591 of a syringe 590, a fixed type small cylinder 593 is provided coaxially with the cylinder 591 so that the external cylinder 591 has a doughnut-shaped space. Within the fixed-type small cylinder 593, a partition 594 and a small plunger 595 are fit, while within the cylinder 591, a doughnut shaped partition 596 and a large plunger 597 are fit. A chamber 598 is formed between the partition 594 of the fixed type small cylinder 593 and the small plunger 595, and a doughnut-shaped chamber 599 is formed between the partition 596 of the cylinder 591 and the large plunger 597. The chambers 598 and 599 are filled with different injection agents.

In the fixed-type small cylinder 593, a closing portion 593a is formed in the neighborhood of the syringe needle 592, and the hollow portion at the end on the side of the syringe needle 592 is a slender terminal passing-through portion 600 communicating with the syringe needle 592. In contact with the right end of the terminal passing-through portion 600, i.e., left end of the closing portion 593a, a vertical through-hole 593b is formed so as to communicate the inside of the external cylinder 591 with the syringe needle 592. At the position slightly apart from the closing portion 593a, a vertical through-hole 593b is formed so as to communicate the inside of the external cylinder 591 with the hollow portion of the fixed type small cylinder 593. The closing portion 593a, which has only to close the hollow portion of the fixed type small cylinder 593 there, may be hollow or solid.

An explanation will be given of one example of the operation of the syringe according to this embodiment.

First, a pushing portion 595' is pushed to push the small plunger 595 toward the syringe needle 592. The pressure in the chamber 598 is enhanced so that the partition 594 moves toward the syringe needle 592. Air which is present on the syringe needle side of the syringe enters the chamber 599 through the through-hole 593c to enhance the pressure in the chamber 599. Correspondingly, the doughnut-shaped partition 596 moves toward the syringe needle. Air on the left side of the partition 596 is externally discharged from an air vent 591d.

When the partition 594 moves to exceed the through-hole 593c, the injection agent in the chamber 598 flows through the through-hole 593c into the chamber 599. Two injection agents are mixed there. With an increase in the pressure, the doughnut-shaped partition 596 further moves toward the syringe needle 592.

When a pushing portion 595' for the small plunger 595 overlaps a pushing portion 597' for the large plunger 597, the large plunger 597 also starts to move toward the syringe needle 597 so that the pressure in the chamber 599 is further enhanced. As a result, the doughnut-shaped portion 596 eventually moves to the left side of the through-hole 593 so that the chamber 599 is communicated with the syringe needle 592 through the through-hole 593b and terminal passing-through portion 600. In this state, with the syringe needle 592 directed upwards, air contained in the chamber 599 is externally discharged. Thereafter, an injection is carried out.

Incidentally, the space from the through-hole 593b to the needle 592 should be made as small possible so that the residue of the injection solution can be minimized.

As described above, in accordance with the present invention, a syringe can be provided which can accommodate one or more injection agents separately and stably preserve them for a long time in a state shut out from the open air. In addition, in use, these injection agents can be immediately given to a patient by a simple operation. Further, not only "mixed injection" can be performed that plural injection agents are mixed and the injection agent thus created is injected can be performed, but also "separate injection" can be performed that plural injection agents can be successively injected in such a manner that an "A" agent is injected and a "B" agent is thereafter injected.

The syringe defined in any claim can be easily manufactured at low cost and also disposable. Particularly, adoption of a structure in which the through-holes formed in a cylinder are coupled with each other by a pipe permits a small-sized syringe to be further manufactured at further low cost. Such a syringe is most suitable to the injection of a small amount. Since the injection agent(s) is not exposed to the open air in operation, there is no fear of pollution.

Although the present invention has been described and illustrated in detail, it should be clearly understood that the same is by way of illustration and example only and is not to be taken by way of limitation, the spirit and scope of the present invention being limited only by the terms of the appended claims.

I claim:

1. A syringe, comprising:
   a cylinder having a connection portion for a syringe needle at one end and an opening at the other end;
   two partitions formed apart from each other within said cylinder, with a hole formed in one of said partitions remote from said connection portion;
   a first small cylinder having a tip which abuts on said one partition and which rotatably abuts on an inside of said cylinder;
   a valve member, residing at the tip of said first small cylinder, for communicating the chamber between said partitions with a chamber formed in said first small cylinder in accord with the hole formed in said partition or separating both chambers from each other in displacement from said hole by rotation of said small cylinder;
   a plunger slidably provided in said first small cylinder; and
   a passage communicating the chamber between said partitions with said connection portion provided when said plunger is moved toward said syringe needle.

2. A syringe according to claim 1, further comprising:
   a second small cylinder having the same structure as said first small cylinder.

3. A syringe according to claim 1, wherein:
   said passage includes an enlarged portion formed adjacent said syringe needle connection portion,
   a cylindrical receiver, accommodated in said enlarged portion, for slidably receiving said partition inside itself, and
   a passing-through passage formed in said receiver.

4. A syringe, comprising:
   a cylinder having a connection portion for a syringe needle at one end and an opening at the other end; and
   a plunger to be inserted into the cylinder from the opening,
   wherein, between said connection portion and said plunger within said cylinder, at least one partition is slidably provided to watertightly divide an internal space into plural chambers of said cylinder,
   an injection agent is accommodated within at least one chamber defined between said partitions or between said partition and said plunger,
   a passage communicating each of said chambers with said connecting portion is provided when said plunger is moved to the side of said syringe needle,
   a pillar member having a hollow portion communicating with said connection portion and protruding into said cylinder to close its tip is further provided,
   said passage consists of said hollow portion of said pillar member and a through-hole formed on the side of said pillar member,
   one of said partitions is slidably fit between an outer periphery of said pillar member and an inner periphery of said cylinder so as to close said through-hole, and
   said passage is opened when said partition slides toward the side of said syringe needle.

5. A syringe, comprising:
   a cylinder, having a connection portion for a syringe needle at a first end and an opening at a second end; and
   a plunger to be inserted into the cylinder from the opening,
   wherein a plurality of partitions are slidably provided between said connection portion and said plunger within said cylinder to divide an internal space of said cylinder into plural watertight chambers,
   wherein between adjacent partitions or between one of said partition and said plunger, two or more chambers are formed,
   wherein the chambers are filled with respective injection agents, and
   a passage formed integrally with the cylinder and communicating each of said chambers with said connection portion is provided without distorting said partitions when said plunger is moved within said cylinder toward said first end, wherein at the center portion of a different partition from said partition, a passage member having a double pipe structure is provided in which an internal cylinder is coaxially held in an external cylinder with a gap therebetween, said passage further includes a hollow portion formed in said internal cylinder so that the side of the syringe needle is opened and the side of the plunger is closed and through-hole is formed on the side of said internal cylinder, a small partition for sealing said gap between said internal and external cylinders and closing said through-hole is slidably fit, and said passage is opened when said partition slides toward said small partition.

6. A syringe, comprising:

a cylinder having a connection portion for a syringe needle at one end and an opening at the other end; and a plunger to be inserted into the cylinder from the opening, wherein between said connection portion and said plunger within said cylinder, at least one partition is slidably provided to watertightly divide the internal space into plural chambers of said cylinder, within at least one chamber between said partitions or between said partition and said plunger, an injection agent is accommodated, a passage communicating each of said chambers with said connecting portion is provided when said plunger is moved to the side of said syringe needle, a passage rod member is provided within said cylinder so a to extend along said cylinder in a longitudinal direction of said cylinder and pass through said partition and said plunger watertightly, wherein one of said passages includes a terminal hollow portion formed in the longitudinal direction of said passage rod member and whose one end communicates with said connection portion, and a first through-hole formed in the neighborhood of the other end of said terminal hollow portion and communicating said hollow portion with the inside of said cylinder, the other passage includes at least one intermediate hollow portion separated from said terminal hollow portion and each other and formed in the longitudinal direction of said passage rod member, and a second through-hole formed in the neighborhood of each of both ends of said intermediate hollow portion and communicating said hollow portion with the inside of said cylinder, and as said plunger moves, said partition is shifted from the position where said passage is closed to the position where it is opened.

7. A syringe, comprising:

a cylinder having a connection portion for a syringe needle at one end and an opening at the other end; and a plunger to be inserted into the cylinder from the opening, wherein between said connection portion and said plunger within said cylinder, at least one partition is slidably provided to divide watertightly the internal space into plural chambers of said cylinder, within at least one chamber between said partitions or between said partition and said plunger, an injection agent is accommodated, a passage communicating each of said chambers with said connecting portion is provided when said plunger is moved to the side of said syringe needle, and said passage consists of at least one pair of through-holes separated from each other by a distance longer than the length of said partition in said cylinder and a pipe connecting the through-holes of each pair with each other.

8. A syringe according to claims 7, wherein:

a passage communicating said pipe with said connection portion is formed at said partition nearest to said syringe needle.

9. A syringe, comprising:

a main cylinder having a connection portion for a syringe needle at one end and an opening at the other end;

a first plunger to be inserted into the cylinder from the opening;

between said connection portion and said plunger within said cylinder, at least two partitions slidably provided to divide an internal space of the main cylinder into at least two watertight chambers adapted to be filled with different injection agents of said cylinder;

at least one passage communicating each of said chambers with said connection portion;

a hole formed in one of said partitions remote from said connection portion;

a first inner cylinder having a tip which abuts on said one partition and which rotatably abuts on the inside of said cylinder; and a valve member disposed at the tip of said inner cylinder.

10. A syringe according to claim 9, wherein:

a second inner cylinder having the same structure as said first inner cylinder is provided in said main cylinder.

11. A syringe according to claim 9, wherein:

an enlarged portion is formed near said syringe needle connection portion and a cylindrical receiver is accommodated in said enlarged portion for slidably receiving said partition inside itself and said passage is formed in the cylindrical receiver.

12. A syringe, comprising:

a main cylinder having a connection portion for a syringe needle at one end and an opening at the other end;

a first plunger to be inserted into the cylinder from the opening;

between said connection portion and said plunger within said cylinder, at least two partitions slidably provided to divide an internal space of the main cylinder into at least two watertight chambers adapted to be filled with different injection agents of said cylinder;

at least one passage communicating each of said chambers with said connection portion; and a pillar member having a hollow portion communicating with said connection portion and protruding into said main cylinder to close its tip, wherein said passage comprises said hollow portion of said pillar member and a first through-hole formed on the side of said pillar member, and one of said partitions being slidably fit between the outer periphery of said pillar member and the inner periphery of said cylinder so as to close said first through-hole.

13. A syringe, comprising:

a main cylinder having a connection portion for a syringe needle at one end and an opening at the other end;

a first plunger to be inserted into the cylinder from the opening;

between said connection portion and said plunger within said cylinder, at least two partitions slidably provided to divide an internal space of the main cylinder into at least two watertight chambers adapted to be filled with different injection agents of said cylinder; and at least one passage communicating each of said chambers with said connection portion, wherein at the center portion of a second partition, a passage having a double pipe structure is provided in which a third internal cylinder is coaxially held in said cylinder with a gap from each other, said second passage further including a hollow portion formed in said third internal cylinder so that the side of the syringe needle is opened and the side of the plunger is closed and a second through-hole formed on the side of said third internal cylinder, and an inner partition for sealing said gap between said two cylinders for closing said second through-hole is slidably fit therein.

14. A syringe, comprising:

a main cylinder having a connection portion for a syringe needle at one end and an opening at the other end;

a first plunger to be inserted into the cylinder from the opening;

between said connection portion and said plunger within said cylinder, at least two partitions slidably provided to divide an internal space of the main cylinder into at least two watertight chambers adapted to be filled with different injection agents of said cylinder;

at least one passage communicating each of said chambers with said connection portion; and a passage rod member is provided within said main cylinder so as to extend along said main cylinder in a longitudinal direction of said main cylinder and passes through said partition and said plunger watertightly, wherein the first passage comprises a terminal hollow portion formed in the longitudinal direction of said passage rod member and whose one end communicates with said connection portion, and a third through-hole formed near the other end of said terminal hollow portion and communicating said hollow portion with the inside of said cylinder, and the second passage comprises at least one intermediate hollow portion separated from said terminal hollow portion and each other, and formed in the longitudinal direction of said passage rod member, and a fourth through-hole formed near each of both ends of said intermediate hollow portion and communicating said hollow portion with the inside of said main cylinder.

15. A syringe, comprising:

a main cylinder having a connection portion for a syringe needle at one end and an opening at the other end;

a first plunger to be inserted into the cylinder from the opening;

between said connection portion and said plunger within said cylinder, at least two partitions slidably provided to divide an internal space of the main cylinder into at least two watertight chambers adapted to be filled with different injection agents of said cylinder; and at least one passage communicating each of said chambers with said connection portion;

wherein said at least one passage comprises at least one pair of through-holes separated from each other by a distance longer than the length of one of said at least two partitions in said main cylinder and a pipe connecting the through-holes of said at least one pair with each other.

16. A syringe according to claim 15, wherein:

said at least one passage communicating said pipe with said connection portion is formed at that one of said at least two partitions which is located nearest to said syringe needle.

17. A syringe according to claim 9, wherein:

within said main cylinder, a hollow fixed type inner cylinder is provided coaxially with said main cylinder at a portion of the hollow portion of said fixed type inner cylinder, a closing portion is formed, and on both sides of said closing portion fifth and sixth through-holes are formed to communicate the hollow portion of said fixed type inner cylinder with that of said cylinder, a partition of said second plunger is fit within said fixed type inner cylinder to form one of said chambers therebetween, and another partition, and the first plunger is fit between said main cylinder and said fixed type inner cylinder to form the other chamber therebetween, the one passage includes a terminal passing-through portion formed within said fixed type inner cylinder and said fifth through-hole, the other passage comprises a sixth through-hole.

18. A syringe according to claim 1, characterized in that another small cylinder having the same structure as said small cylinder is provided in said cylinder.

* * * * *